(12) United States Patent
Rabnawaz

(10) Patent No.: US 11,440,868 B2
(45) Date of Patent: Sep. 13, 2022

(54) REVERSIBLE ADHESIVE COMPOSITIONS, RELATED ARTICLES, AND RELATED METHODS

(71) Applicant: BOARD OF TRUSTEES OF MICHIGAN STATE UNIVERSITY, East Lansing, MI (US)

(72) Inventor: Muhammad Rabnawaz, East Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 210 days.

(21) Appl. No.: 16/935,364

(22) Filed: Jul. 22, 2020

(65) Prior Publication Data

US 2021/0024452 A1 Jan. 28, 2021

Related U.S. Application Data

(60) Provisional application No. 62/877,001, filed on Jul. 22, 2019.

(51) Int. Cl.

| | |
|---|---|
| *C07C 69/01* | (2006.01) |
| *C07C 43/16* | (2006.01) |
| *C09J 133/08* | (2006.01) |
| *C09J 133/12* | (2006.01) |
| *B32B 7/12* | (2006.01) |
| *B32B 5/02* | (2006.01) |
| *B32B 7/06* | (2019.01) |
| *B32B 15/14* | (2006.01) |
| *B32B 27/10* | (2006.01) |
| *B32B 9/06* | (2006.01) |
| *B32B 15/10* | (2006.01) |
| *B32B 15/12* | (2006.01) |
| *B32B 17/10* | (2006.01) |
| *B32B 27/08* | (2006.01) |
| *B32B 27/12* | (2006.01) |
| *B32B 29/02* | (2006.01) |
| *B32B 21/04* | (2006.01) |
| *B32B 37/12* | (2006.01) |

(52) U.S. Cl.
CPC ............... *C07C 69/01* (2013.01); *B32B 7/12* (2013.01); *B32B 21/042* (2013.01); *B32B 37/12* (2013.01); *C07C 43/16* (2013.01); *C09J 133/08* (2013.01); *C09J 133/12* (2013.01); *B32B 2309/125* (2013.01); *B32B 2419/00* (2013.01)

(58) Field of Classification Search
None
See application file for complete search history.

(56) References Cited

U.S. PATENT DOCUMENTS

2018/0346764 A1* 12/2018 Himmelberger ........... C09J 4/00

FOREIGN PATENT DOCUMENTS

| WO | WO-2020/142578 | 7/2020 |
| WO | WO-2020/160089 | 8/2020 |

OTHER PUBLICATIONS

Urban et al., "Key-and-Lock Commodity Self-Healing Copolymers," *Science*, 362:220-25 (Oct. 12, 2018).

* cited by examiner

*Primary Examiner* — Sheeba Ahmed
(74) *Attorney, Agent, or Firm* — Marshall, Gerstein & Borun LLP

(57) ABSTRACT

The disclosure relates to a reversible adhesive composition including a copolymer between a vinyl spacer monomer unit and a vinyl reversible binder monomer unit. Each monomer unit can be based on acrylate monomer, a vinyl ester monomer, or a vinyl ether monomer, with the spacer monomer unit generally having a shorter pendant chain (such as 1-3 carbon atoms) and the reversible binder monomer unit having a longer pendant chain (such as 3-20 carbon atoms). A corresponding article includes first and second surfaces (or substrates) that are in contact with and bonded to the reversible adhesive composition at an interface therebetween. The reversible adhesive composition generally involves non-covalent and/or non-ionic bonding forces, for example H-bonding, permanent dipole, electron donor-acceptor moieties, and/or van der Waals forces, between the copolymer chains. The first and second surfaces can be repeatedly bonded, separated, and re-bonded while retaining the adhesive strength of the reversible adhesive composition.

24 Claims, 7 Drawing Sheets

REVERSIBLE ADHESIVE COMPOSITIONS, RELATED ARTICLES, AND RELATED METHODS

CROSS REFERENCE TO RELATED APPLICATION

Priority is claimed to U.S. Provisional Application No. 62/877,001 (filed Jul. 22, 2019), which is incorporated herein by reference in its entirety.

STATEMENT OF GOVERNMENT INTEREST

None.

BACKGROUND OF THE DISCLOSURE

Field of the Disclosure

The disclosure relates to a reversible adhesive composition including a copolymer between a vinyl spacer monomer unit and a vinyl reversible binder monomer unit. Each monomer unit can be based on acrylate monomer, a vinyl ester monomer, or a vinyl ether monomer, with the spacer monomer unit generally having a shorter pendant chain and the reversible binder monomer unit having a longer pendant chain. A corresponding article includes first and second surfaces (or substrates) that are in contact with and reversibly bonded to the reversible adhesive composition at an interface therebetween.

Brief Description of Related Technology

Currently, several approaches are commonly used to assemble various parts and make a functional system, including snap fit, permanent adhesives, nails, screws and bolts. However, with the exception of key-and-lock fit and bolts, in other cases, it is challenging to disassemble the jointed objects without damage or intensive efforts. Consequently, the current joints technologies are suitable primarily for single-use applications. While key-and-lock fit and bolts are reversible, these are less economical owing to the costly incorporation of these into a system.

Adhesives are typically inexpensive materials commonly used to join objects and build structures. The current adhesives used for structural and semi-structural applications (e.g., holding mild to heavy loads) are thermosets. These thermosets, once applied, become challenging to debond. This non-reversible nature prohibits their use where reversible assemblies are required. The only class of adhesives that are reversible are pressure sensitive adhesives (PSA), but these often lack strength for holding mild and heaving objects.

Reversible adhesives are highly desirable for a wide range of applications. Research is ongoing to develop reversible adhesives (R-ADHs) that can be reversibly attached to adherends/substrates. However, with the exception of pressure-sensitive adhesives (PSA), most R-ADHs rely on external stimuli. For example, hot-melt adhesives are widely used as thermal glues, which can undergo debonding upon thermal treatment to melt the adhesives. Besides thermal treatment, other stimuli-responsive polymers (e.g., pH-, pressure-, and light-responsive materials) can also serve as reversible glues. However, this class of reversible glues relies on external stimuli, which involves complex treatment and specialized equipment to achieve the debonding processes.

Pressure-sensitive adhesives (PSAs) are a special class of reversible adhesive (R-ADH) materials, with which joints can be formed without the need for an external stimulant, with the exception of mild pressure which is typically applied for a short duration (1-5 s) to enforce the joints. The working principle regarding PSAs is based on the facile formation of joints that is ensured by the high molecular mobility and fluidity of the adhesives under applied pressure. Meanwhile, debonding under stress is dependent by the intermolecular cohesive strength and elasticity of the materials. Challenges encountered with PSAs include their poor thermal resistance and poor performance in low-stress applications such a sticky notes and labeling. The latest generation of PSAs exhibits improved stress resistance via the use of appropriate primers and adhesion promoters for semi-structural applications. However, these materials are primarily targeted for single-use applications.

Intrinsic self-healing materials are a unique class of materials that can undergo repair in the presence or absence of external stimuli, and they have been extensively investigated for anti-rust applications. Such self-healing materials rely on reversible covalent and non-covalent interactions, such as hydrogen bonding, high-valence metal chelation, host-guest interactions, and dynamic covalent bonds (disulfide-bonds, acylhydrazone bonds, nitroxides, dynamic urea bonds, and those formed via Diels-Alder addition or transesterification reactions). However, this technique relies on stimuli to achieve debonding and also requires thermal, solvent, or other treatment to promote re-bonding with few exceptions, such as dynamic urea bonds. However, the problem with dynamic urea systems could be that they are too weak to withstand stresses and thus they would be prone to cohesive failure during routine as adhesives. Thus far, the focus for self-healing materials is their use for anti-corrosion coatings and aerospace applications because they self-heal the scratches through zipping the cracks from both sides.

SUMMARY

There is a strong need for materials for various applications that can assemble objects in seconds-to-minutes by applying only mild pressure with considerable strength to support loads and stresses varying from low-to-heavy. More particularly, considering the increasing demand of automation and rapid assembly and disassembly in various sectors ranging from production lines to supply/distribution, civil to military fast track constructions, and packaging to non-packaging applications, there is a need for materials that facilitate reversible joints with good structural and thermal performance. Reversible adhesives addressing these needs also can promote the reuse and thus reduce the waste associated with such products.

The present disclosure addresses these needs with adhesives that adhere to each other only (i.e., a self-adhesive material) via reversible non-covalent bonding, thus providing a means for reversible assembly and disassembly of various articles. The disclosed adhesives, which can be termed reversible self-adhesives (RS-ADH), can be used to reversibly join substrate surface in various assemblies with a tunable adhesive strength, for example with reversible bonding and debonding under ambient conditions (e.g., about 20-30° C.). The disclosed adhesives can be bonded and debonded essentially instantaneously for virtually unlimited cycles without the need for any external stimulant. The examples below illustrate the disclosed adhesives and related articles with a poly(alkyl acrylate-co-methacrylate) reversible adhesive copolymer have tunable cohesive and adhesive strengths.

In one aspect, the disclosure relates to an article comprising: a first surface; a second surface different from the first surface; and a reversible adhesive composition in contact with and bonded to the first surface and the second surface at an interface of the article. The reversible adhesive composition comprises a copolymer comprising: a vinyl spacer monomer unit (e.g., as a first monomer unit) comprising at least one of (i) a pendant carboxylate group with a carbonyl carbon backbone attachment and in the form of an acid, a salt (e.g., alkali metal salt such as Na, K), an ester with 1 to 3 carbon atoms in a corresponding ester group (e.g., linear or branched, substituted or unsubstituted methyl, ethyl, or propyl ester), and combinations thereof (e.g., multiple different pendant carboxylate groups in the copolymer), (ii) a pendant carboxylate group with an ester oxygen backbone attachment and having a hydrocarbon tail group with 1 to 3 carbon atoms (e.g., linear or branched, substituted or unsubstituted methyl, ethyl, or propyl group), (iii) a pendant ether group with an ether oxygen backbone attachment and having a hydrocarbon tail group with 1 to 3 carbon atoms (e.g., linear or branched, substituted or unsubstituted methyl, ethyl, or propyl group); and a vinyl reversible binder monomer unit (e.g., as a second monomer unit) comprising at least one of (i) a pendant carboxylate group with a carbonyl carbon backbone attachment and in the form of an ester having 3 to 20 carbon atoms in a corresponding ester group (e.g., linear or branched, substituted or unsubstituted hydrocarbon group such as alkyl), (ii) a pendant carboxylate group with an ester oxygen backbone attachment and having a hydrocarbon tail group with 3 to 20 carbon atoms (e.g., linear or branched, substituted or unsubstituted hydrocarbon group such as alkyl), and (iii) a pendant ether group with an ether oxygen backbone attachment and having a hydrocarbon tail group with 3 to 20 carbon atoms (e.g., linear or branched, substituted or unsubstituted hydrocarbon group such as alkyl); wherein the vinyl spacer monomer unit and the vinyl reversible binder monomer unit are different. For example the vinyl reversible binder monomer unit generally has a longer pendant chain than the vinyl spacer monomer unit, such as being longer by at least 1, 2, 3, 4, 6, 8, or 10 carbon atoms and/or up to 4, 6, 8, 10, 14, or 18 carbon atoms.

The article is generally an assembled, multipart article with reversibly joined surfaces using the reversible adhesive in any of its disclosed embodiments. The first and second surfaces can be surfaces of the same or different substrate, and they are generally in an opposing orientation relative to each other, with the reversible adhesive composition situated at an interface of the article between the first and second surfaces. The reversible adhesive composition generally involves non-covalent and/or non-ionic bonding forces, for example H-bonding, permanent dipole, electron donor-acceptor moieties, and/or van der Waals forces, between the copolymer chains. Such forces act within the bulk of the reversible adhesive composition and between adjacent/touching reversible adhesive composition surfaces (e.g., when separate adhesive composition surfaces are contacted to form the article with joined surfaces). Such forces are generally stronger within the bulk of the composition and relatively weaker at the interface between adjacent/touching reversible adhesive composition surfaces, although the weaker forces at the interfacial locations are still sufficiently strong to bind the surfaces together. The relatively weaker forces at the interface allow the two surfaces to be repeatedly separated (with application of sufficient force) and re-joined at essentially the same location, thus leaving the reversible adhesive composition originally present on each surface essentially intact. There is no observed thread or fiber formation during the separation/de-bonding process. Accordingly, even when the article is in assembled form, the reversible adhesive composition between the first and second surfaces can be itself characterized as having an internal interface between original portions/coatings of the reversible adhesive composition on each of the corresponding first and second surfaces. Such an internal interface within the reversible adhesive composition generally corresponds to the location where repeated bonding/de-bonding occurs. The reversible adhesive composition originally present on each surface can include the same or different copolymer relative to a corresponding surface to which it can be reversibly joined. When different reversible adhesive compositions/copolymers are used for complementary surfaces to be joined, one copolymer may have electron donating species and the other may have electron acceptor species to form a stronger reversible bond.

In another aspect, the disclosure relates to a reversible adhesive composition comprising a copolymer comprising: a vinyl spacer monomer unit (e.g., as a first monomer unit) comprising at least one of (i) a pendant carboxylate group with a carbonyl carbon backbone attachment and in the form of an acid, a salt (e.g., alkali metal salt such as Na, K), an ester with 1 to 3 carbon atoms in a corresponding ester group (e.g., linear or branched, substituted or unsubstituted methyl, ethyl, or propyl ester), and combinations thereof (e.g., multiple different pendant carboxylate groups in the copolymer), (ii) a pendant carboxylate group with an ester oxygen backbone attachment and having a hydrocarbon tail group with 1 to 3 carbon atoms (e.g., linear or branched, substituted or unsubstituted methyl, ethyl, or propyl group), (iii) a pendant ether group with an ether oxygen backbone attachment and having a hydrocarbon tail group with 1 to 3 carbon atoms (e.g., linear or branched, substituted or unsubstituted methyl, ethyl, or propyl group); and a vinyl reversible binder monomer unit (e.g., as a second monomer unit) comprising at least one of (i) a pendant carboxylate group with a carbonyl carbon backbone attachment and in the form of an ester having 3 to 20 carbon atoms in a corresponding ester group (e.g., linear or branched, substituted or unsubstituted hydrocarbon group such as alkyl), (ii) a pendant carboxylate group with an ester oxygen backbone attachment and having a hydrocarbon tail group with 3 to 20 carbon atoms (e.g., linear or branched, substituted or unsubstituted hydrocarbon group such as alkyl), and (iii) a pendant ether group with an ether oxygen backbone attachment and having a hydrocarbon tail group with 3 to 20 carbon atoms (e.g., linear or branched, substituted or unsubstituted hydrocarbon group such as alkyl); wherein the vinyl spacer monomer unit and the vinyl reversible binder monomer unit are different. For example the vinyl reversible binder monomer unit generally has a longer pendant chain than the vinyl spacer monomer unit, such as being longer by at least 1, 2, 3, 4, 6, 8, or 10 carbon atoms and/or up to 4, 6, 8, 10, 14, or 18 carbon atoms.

In another aspect, the disclosure relates to a method for forming an article, the method comprising: providing a first surface comprising at least a portion of a reversible adhesive composition according to any of the variously disclosed embodiments thereon; providing a second surface different from the first surface and comprising at least a portion of the reversible adhesive composition thereon; and contacting the reversible adhesive composition of the first surface with the reversible adhesive composition of the second surface at an interface for a time and at a pressure sufficient to bond the first surface and the second surface together at the interface with the reversible adhesive composition there between, thereby forming a joined article. During a typical bonding or re-bonding step, the ambient temperature is suitably be greater than the glass transition temperature of the copolymer in the reversible adhesive composition.

In another aspect, the disclosure relates to a method for de-bonding and optionally re-bonding an article, the method comprising: providing the (joined) article according to any of the variously disclosed embodiments; and applying a force sufficient to separate the first surface from the second surface while retaining at least a portion of the reversible adhesive composition on each of the first surface and the second surface. In a refinement, the method further comprises: contacting the reversible adhesive composition of the separated first surface with the reversible adhesive composition of the separated second surface at an interface for a time and pressure sufficient to re-bond the first surface and the second surface together at the interface with the reversible adhesive composition therebetween, thereby re-forming the (joined) article.

In another aspect, the disclosure relates to an article or a kit comprising: a first surface; a first reversible adhesive composition on the first surface (e.g., coated/bound thereto as a film or coating); a second surface different from the first surface; and a second reversible adhesive composition on the second surface (e.g., coated/bound thereto as a film or coating). The first and second reversible adhesive compositions can be according to any of the disclosed embodiments. Suitably, the first and second reversible adhesive compositions have the same chemical composition, but are positioned at different locations/surfaces. In other cases, the first and second reversible adhesive compositions can have the different chemical compositions, but which have compatible reversible binder monomer units for binding between each other. The first and second reversible adhesives are adapted to bond to each other when contacted at an interface (e.g., for sufficient time/under sufficient pressure). The first and second surfaces can be from the same or different substrates.

In another aspect, the disclosure relates to uses and articles in which the reversible adhesive composition according to the disclosure is used as a stand-alone material. For example, the substrates to be joined in various articles can include the reversible adhesive composition as the bulk material of the substrate, and the external surface of the substrate is also formed from the reversible adhesive composition, thus allowing separate substrates to be reversibly joined at their external surfaces. For example, the reversible adhesive composition can be used as a stand-alone 3D printing material. A single, unitary object can be 3D-printed using the reversible adhesive composition. In such cases, adjacent printed layers (e.g., in a layer-by-layer printed structure) can exhibit improved interlayer adhesion based on the reversible adhesive composition, thereby providing improved structural integrity for the final printed object. Objects that are separately printed from the reversible adhesive composition can be reversibly joined at their external surfaces to form an article. In a related 3D-printing use, the reversible adhesive composition can be used as an external coating on a conventional 3D printing polymer/resin (e.g., polylactic acid or otherwise). Similarly, objects that are separately printed and include an external reversible adhesive composition coating can be reversibly joined at their external surfaces to form an article.

Various refinements of the disclosed reversible adhesive compositions, articles, kits, and methods are possible.

In a refinement, the first surface and the second surface are capable of being separated from each other (i) without damage to the first surface or the second surface, and (ii) with at least a portion of the reversible adhesive composition remaining each of the first surface and the second surface; and the separated first surface and the separated second surface are capable of being rejoined at the interface with the reversible adhesive composition in contact with and bonded to the first surface and the second surface at the interface. The joined surfaces can be separated with application of a non-destructive level of force/stress, for example to pull them apart. The separated surfaces can subsequently be rejoined by re-contacting the surfaces at the interface with the reversible adhesive composition there between, for example with application of minor pressure. Specifically, the first and second surfaces (or their corresponding substrates) can be each initially providing with an external film, coating, discrete dot, or other layer of the reversible adhesive composition, and reversible bonding occurs when two opposing copolymer-copolymer surfaces of respective opposing films, coatings, dots, or other layers are contacted. The layer of the reversible adhesive composition can be initially provided its corresponding surface or substrate by any suitable method such as solvent casting, hot-melt application, water-borne formulation application, powder-melt application, etc. The joined surfaces can be repeatedly separated and re-joined without substantially reducing the strength of the interface bonding the two surfaces. For example, the interface bonding/joining the two surfaces can have a yield strength of at least 80% (e.g., at least 80, 85, 90, or 95% and/or up to 90, 95, 98, or 99%) relative to initial yield strength after 5, 10, 20, 50, or 100 cycles of separation/re-joining, where the yield strength corresponds to the minimum load required to separate joined surfaces, and the initial yield strength is the yield strength after the first joining of the surfaces. The absolute yield strength for typical joined surfaces is not particularly limited, but it can range from about 0.01 MPa to 500 MPa (e.g., at least 0.01, 0.1, 0.5, 1, 2, 5, or 10 MPa and/or up to 5, 10, 20, 50, 100, 200, to 500 MPa). The pressure required to (re)bond separated surfaces/substrates is not particularly limited, but it can range from about 0.1 N to 400 N (e.g., at least 0.1, 0.5, 1, 2, 5, 10, 20, 30, 40, or 50 N and/or up to 20, 40, 60, 80, 100, 200, or 400 N). The contact time for applied pressure to (re)bond is not particularly limited, but it can range from about 2 sec to 600 sec (e.g., at least 2, 5, 10, 20, or 30 sec and/or up to 30, 60, 120, 240, or 600 sec).

In a refinement, the vinyl spacer monomer unit has a structure corresponding to a polymerization product (e.g., free radical or controlled radical polymerization or other suitable polymerization methods) of a vinyl spacer monomer according to formula I.A (e.g., pendant carboxylate group with a carbonyl carbon backbone attachment): $CH_2=CR'_1—C(=O)O—R'2$ (I.A). $R'_1$ is selected from hydrogen (H) and a methyl group; and $R'_2$ is selected from hydrogen (H), an alkali metal (e.g., Na, K), and hydrocarbons containing from 1 to 3 carbon atoms. The hydrocarbons can be linear, branched, substituted, and/or unsubstituted, etc., for example including methyl, ethyl, propyl, or isopropyl groups and in particular having only 1 or 2 carbon atoms, optionally substituted with one or more N-, O-, P-, and/or S-containing functional groups. Selection of $R'_1$ as H corresponds to an acrylate/acrylic acid functional group. Selection of as $CH_3$ corresponds to a methacrylate/methacrylic acid functional group.

In a refinement, the vinyl spacer monomer unit has a structure corresponding to a polymerization product (e.g., free radical or controlled radical polymerization or other suitable polymerization methods) of a vinyl spacer monomer according to formula II.A (e.g., pendant carboxylate group with an ester oxygen backbone attachment): $CH_2=CR'_3—OC(=O)—R'_4$ (II.A). $R'_3$ is selected from hydrogen (H) and a methyl group; and $R'_4$ is selected from hydrocarbons containing from 1 to 3 carbon atoms. The hydrocarbons can be linear, branched, substituted, and/or unsubstituted, etc., for example including methyl, ethyl, propyl, or isopropyl groups and in particular having only 1 or 2 carbon atoms, optionally substituted with one or more N-, O-, P-, and/or S-containing functional groups. The monomer according to formula II.A generally corresponds to a vinyl ester monomer, for example vinyl acetate or longer-chain and/or substituted analogs thereof.

In a refinement, the vinyl spacer monomer unit has a structure corresponding to a polymerization product (e.g., free radical or controlled radical polymerization or other suitable polymerization methods) of a vinyl spacer monomer according to formula III.A (e.g., pendant ether group with an ether oxygen backbone attachment): $CH_2=CR'_5—O—R'_6$ (III.A). $R'_5$ is selected from hydrogen (H) and a methyl group; and $R'_6$ is selected from hydrocarbons containing from 1 to 3 carbon atoms. The hydrocarbons can be linear, branched, substituted, and/or unsubstituted, etc., for example including methyl, ethyl, propyl, or ispropyl groups and in particular having only 1 or 2 carbon atoms, optionally substituted with one or more N-, O-, P-, and/or S-containing functional groups. The monomer according to formula III.A generally corresponds to a vinyl ether monomer, for example vinyl methyl ether or longer-chain and/or substituted analogs thereof.

In a refinement, the vinyl reversible binder monomer unit has a structure corresponding to a polymerization product (e.g., free radical or controlled radical polymerization or other suitable polymerization methods) of a vinyl reversible binder monomer according to formula I.B (e.g., pendant carboxylate group with a carbonyl carbon backbone attachment): $CH_2=CR_1—C(=O)O—R_2$ (I.B). $R_1$ is selected from hydrogen (H) and a methyl group; and $R_2$ is selected from hydrocarbons containing from 3 to 20 carbon atoms. The hydrocarbons can be linear, branched, substituted, unsubstituted, cyclic, aliphatic, or aromatic, saturated, and/or unsaturated, etc., for example having at least 3, 4, 5, 6, 8, 10, or 12 and/or up to 8, 10, 12, 14, 16, 18, or 20 carbon atoms, optionally substituted with one or more N-, O-, P-, and/or S-containing functional groups or atoms. Example functional groups present in $R_2$ can include one or more of halogen atoms, alkyl groups (e.g., as a chain or a terminal $CH_3$ group, such as at the end of a chain or a branch), aryl groups, hydroxyl groups, amine groups, nitrile groups, ester groups, carboxylic acid groups, aldehyde groups, ketone groups, ether groups, and combinations thereof. Selection of $R_1$ as H corresponds to an acrylate/acrylic acid functional group. Selection of $R_1$ as $CH_3$ corresponds to a methacrylate/methacrylic acid functional group.

In a refinement, the vinyl reversible binder monomer unit has a structure corresponding to a polymerization product (e.g., free radical or controlled radical polymerization or other suitable polymerization methods) of a vinyl reversible binder monomer according to formula II.B (e.g., pendant carboxylate group with an ester oxygen backbone attachment): $CH_2=CR_3—OC(=O)—R_4$ (II.B). $R_3$ is selected from hydrogen (H) and a methyl group; and $R_4$ is selected from hydrocarbons containing from 3 to 20 carbon atoms. The hydrocarbons can be linear, branched, substituted, unsubstituted, cyclic, aliphatic, or aromatic, saturated, and/or unsaturated, etc., for example having at least 3, 4, 5, 6, 8, 10, or 12 and/or up to 8, 10, 12, 14, 16, 18, or 20 carbon atoms, optionally substituted with one or more N-, O-, P-, and/or S-containing functional groups or atoms. Example functional groups present in $R_4$ can include one or more of halogen atoms, alkyl groups (e.g., as a chain or a terminal $CH_3$ group, such as at the end of a chain or a branch), aryl groups, hydroxyl groups, amine groups, nitrile groups, ester groups, carboxylic acid groups, aldehyde groups, ketone groups, ether groups, and combinations thereof. The monomer according to formula II.B generally corresponds to a vinyl ester monomer, for example vinyl butyrate or longer-chain and/or substituted analogs thereof.

In a refinement, the vinyl reversible binder monomer unit has a structure corresponding to polymerization product (e.g., free radical or controlled radical polymerization or other suitable polymerization methods) of a vinyl reversible binder monomer according to formula III.B (e.g., pendant ether group with an ether oxygen backbone attachment): $CH_2=CR_5—O—R_6$ (III.B). $R_5$ is selected from hydrogen (H) and a methyl group; and $R_6$ is selected from hydrocarbons containing from 3 to 20 carbon atoms. The hydrocarbons can be linear, branched, substituted, unsubstituted, cyclic, aliphatic, or aromatic, saturated, and/or unsaturated, etc., for example having at least 3, 4, 5, 6, 8, 10, or 12 and/or up to 8, 10, 12, 14, 16, 18, or 20 carbon atoms, optionally substituted with one or more N-, O-, P-, and/or S-containing functional groups or atoms. Example functional groups present in $R_6$ can include one or more of halogen atoms, alkyl groups (e.g., as a chain or a terminal $CH_3$ group, such as at the end of a chain or a branch), aryl groups, hydroxyl groups, amine groups, nitrile groups, ester groups, carboxylic acid groups, aldehyde groups, ketone groups, ether groups, and combinations thereof. The monomer according to formula III.B generally corresponds to a vinyl ether monomer, for example vinyl butyl ether or longer-chain and/or substituted analogs thereof.

In any of the foregoing refinements, more than one type of vinyl spacer monomer unit can be included and/or more than one type of vinyl reversible binder monomer unit can be included. For example, more than one type of vinyl spacer monomer according to any of formulas I.A, II.A, or III.A can be used. Similarly, more than one type of vinyl reversible binder monomer according to any of formulas I.B, II.B, or III.B can be used. When one monomer is an acrylate-based monomer and another monomer is a vinyl ester- or vinyl-ether based monomer, the resulting copolymer can include alternating segments. When both monomers are acrylate-based monomers, or both monomers vinyl ester- or vinyl-ether based monomers, the resulting copolymer can include statistical/random segments. Suitably, at least one monomer includes a pendant methyl group, which is useful to control the glass transition temperature of the copolymer to be within a desired range for a reversible adhesive. This can suitably be the case when the methyl group is incorporated into the spacer monomer unit, such as when $R'_1$, $R'_3$, or $R'_5$ is methyl in formula I.A, II.A, or III.A, respectively. In such cases, $R_1$, $R_3$, or $R_5$ can be hydrogen in formula I.B, II.B, or III.B, respectively. Alternatively, the methyl group can be incorporated into the binder monomer unit, with the analogous positions on the spacer monomer unit being hydrogen.

In a refinement, the vinyl spacer monomer units are present in the copolymer in a range from 10 mol. % to 90 mol. % relative to total vinyl spacer monomer units and vinyl reversible binder monomer units combined; and the vinyl reversible binder monomer units are present in the copolymer in a range from 10 mol. % to 90 mol. % relative to total vinyl spacer monomer units and vinyl reversible binder monomer units combined. More generally, the vinyl spacer monomer units can be present in an amount of at least 10, 20, 30, 40, 45, 50, 55, 60, or 70 mol. % and/or up to 40, 45, 50, 55, 60, 70, 80, or 90 mol. %. Likewise, the vinyl reversible binder monomer units can be present in an amount of at least 10, 20, 30, 40, 45, 50, 55, 60, or 70 mol. % and/or up to 40, 45, 50, 55, 60, 70, 80, or 90 mol. %. Suitably, at least 50, 60, 70, 80, 90, or 95 mol. % and/or up to 70, 80, 90, 95, or 98 mol. % of the copolymer corresponds to total vinyl spacer monomer units and vinyl reversible binder monomer units. Similar ranges can apply on a weight basis for the respective monomer units.

In a refinement, the copolymer further comprises: a vinyl crosslinking monomer unit (e.g., as a third monomer unit); and crosslinks between copolymer chains via the vinyl crosslinking monomer unit. The vinyl crosslinking monomer unit can be derived from a vinyl monomer with a pendant hydroxyl group or amine group, for example for crosslinking with a diisocyanate, triisocyanate, or other polyisocyanate, thus imparting urethane or urea crosslinks into the copolymer. Examples of suitable vinyl crosslinking monomers include 2-hydroxyethyl (meth)acrylate, 2-aminoethyl (meth)acrylate, etc. Suitable polyisocyanates can include any aromatic, alicyclic, and/or aliphatic isocyanates having at least two (e.g., 2-4) reactive isocyanate groups (—NCO). Examples of specific polyisocyanates include 1,5-naphthylene diisocyanate, 4,4'-diphenylmethane diisocyanate (MDI), hydrogenated MDI, xylene diisocyanate (XDI), tetramethylxylol diisocyanate (TMXDI), 4,4'-diphenyl-dimethylmethane diisocyanate, di- and tetraalkyl-diphenylmethane diisocyanate, 4,4'-dibenzyl diisocyanate, 1,3-phenylene diisocyanate, 1,4-phenylene diisocyanate, one or more isomers of tolylene diisocyanate (TDI, such as toluene 2,4-diisocyanate), 1-methyl-2,4-diiso-cyanatocyclohexane, 1,6-diisocyanato-2,2,4-trimethyl-hexane, 1,6-diisocyanato-2,4,4-trimethylhexane, 1-iso-cyanatomethyl-3-isocyanato-1,5,5-trimethylcyclohexane, chlorinated and brominated diisocyanates, phosphorus-containing diisocyanates, 4,4'-diisocyanatophenyl-perfluoroethane, tetramethoxybutane 1,4-diisocyanate, butane 1,4-diisocyanate, hexane 1,6-diisocyanate (or hexamethylene diisocyanate; HDI), HDI dimer (HDID), HDI trimer (HDIT), HDI biuret, 1,5-pentamethylene diisocyanate (PDI), PDID (dimer of PDI), PDIT (trimer of PDI), PDI biuret, dicyclohexylmethane diisocyanate, cyclohexane 1,4-diisocyanate, ethylene diisocyanate, phthalic acid bisisocyanatoethyl ester, 1-chloromethylphenyl 2,4-diisocyanate, 1-bromomethylphenyl 2,6-diisocyanate, 3,3-bischloromethyl ether 4,4'-diphenyldiisocyanate, trimethylhexamethylene diisocyanate, 1,4-diisocyanato-butane, 1,2-diisocyanatododecane, and combinations thereof. The vinyl crosslinking monomer unit can be incorporated into the copolymer in an amount from 0.5 mol. % to 20 mol. % (e.g., at least 0.5, 1, 2, 3, 4, 5, or 8 mol. % and/or up to 4, 6, 8, 10, 12, 16, or 20 mol. %), for example based on (i) total vinyl spacer monomer units and vinyl reversible binder monomer units combined or (ii) total vinyl monomer units combined.

In a refinement, the copolymer of the reversible adhesive composition comprises statistical segments with the vinyl spacer monomer units and the vinyl reversible binder monomer unit. The copolymer can include statistical or random copolymer segments (e.g., ABAABBBAABAABB), for example when the spacer and reversible binder are based on acrylate monomers. The copolymer can be formed substantially entirely as a statistical or random copolymer. In some embodiments, only a portion of the copolymer includes the spacer and reversible binder units, for example when the copolymer includes (block) portions of the copolymer that could be non-binding (e.g., formed from spacer units or otherwise) joined by segments of statistical/random spacer/reversible binder units. Non-binding portions of the copolymer can be 0-90 mol. % or wt. %, for example about 5 or 10 to 30 or 40 mol. % or wt. %. In some embodiments, a single copolymer can include some blocks having one kind of binding interactions (e.g., van der Waals) and some blocks having another kind of binding interactions (e.g. dipole moment).

In a refinement, the copolymer of the reversible adhesive composition comprises alternating segments between the vinyl spacer monomer units and the vinyl reversible binder monomer unit. The copolymer can include alternating copolymer segments (e.g., ABABABABAB), for example when the spacer is based on an acrylate monomer and the reversible binder is based on a non-acrylate monomer such as vinyl ether or vinyl ester. The copolymer can be formed substantially entirely as an alternating copolymer. The alternating structure generally has a 1:1 molar ratio between the two alternating units in the copolymer, although the ratio of monomers in the reactant/feed can vary. Similar to above, in some embodiments, only a portion of the copolymer includes the spacer and reversible binder units, for example when the copolymer includes (block) portions of the copolymer that could be non-binding (e.g., formed from spacer units or otherwise) joined by segments of alternating 1:1 spacer/reversible binder units. Non-binding portions of the copolymer can be 0-90 mol. % or wt. %, for example about 5 or 10 to 30 or 40 mol. % or wt. %. Such structures can be formed using a semi-batch synthesis or selective polymerization in the presence of more than 2 monomers.

In a refinement, the copolymer of the reversible adhesive composition has a glass transition temperature in a range from −10° C. to 18° C. More generally, the copolymer can have a glass transition temperature of at least −20° C., −10° C., 0° C., 10° C., 20° C., 30° C. or 40° C. and/or up to 10° C., 18° C., 20° C., 40° C., 60° C., or 80° C. When the reversible adhesive composition is intended to be used (e.g., bonded and/or de-bonded) at ambient temperature conditions (e.g., about 20-25° C.), the glass transition temperature can be in a range from −20° C. to 10° C. or −10° C. to 18° C. such that ambient heat in combination with mild applied pressure is typically sufficient to effect bonding. In embodiments where the glass transition temperature is above ambient temperature conditions, the glass transition temperature can be in a range from 30° C. to 80° C. or 40° C. to 60° C. such that applied heat would be used in combination with pressure to effect bonding.

In a refinement, the copolymer of the reversible adhesive composition has a molecular weight in a range from 1,500 g/mol to 2,000,000 g/mol or 25,000 g/mol to 200,000 g/mol. In various embodiments, the molecular weight can be at least 1,500, 5,000, 10,000, 25,000, or 50,000 and/or up to 50,000, 100,000, 200,000, 500,000, or 2,000,000 g/mol. The molecular weight can be expressed as a number-average or weight-average value in the units of gram/mole (g/mol).

In a refinement, the reversible adhesive composition has a thickness between the first surface and the second surface in a range from 0.005 μm to 5000 μm or 1 μm to 100 μm. In various embodiments, the thickness can be at least 0.005, 0.01, 0.1, 1, 2, 5, 10, 20, 50, or 100 μm and/or up to 10, 20, 50, 100, 200, 500, 1000, 2000, or 5000 The foregoing ranges similarly can apply to individual layers of the reversible adhesive composition on their respective surfaces before being joined/bonded together. The coatings can be cast, sprayed, spin-coated, etc., and multiple coatings can be applied to achieve any desired thickness.

In a refinement, the reversible adhesive composition further comprises additives. The additives can be present in admixture with the copolymer of the reversible adhesive composition, but they are generally not (covalently) bonded thereto. Examples of additives can include silica particles and polystyrene, both of which can be particularly useful for high-temperature applications and/or adhesion to substrates different in chemical nature than the adhesives. For example, in a blend of polystyrene and poly(methylmethacrylate-co-n-butylacrylate) (p(MMA/nBA)), the domains of the polystyrene do not soften until about 100° C., while the p(MMA/nBA) softens at about 40° C. and thus the polystyrene additive function as physical crosslinking agent. In addition, the use of polystyrene in the (p(MMA/nBA)) will enhance adhesion with polystyrene films as polystyrene (e.g., in substrate/film) and polystyrene (e.g., in the adhesive mixture) have an affinity for each other. Similarly, other polymers can be added to increase adhesion with other substrates. In certain cases, compatibalizers can be used with physical crosslinking agents are added to reduce phase separation between the crosslinking agents and the reversible adhesive matrix.

In a refinement, the first surface is a surface of a first substrate; and the second surface is a surface of a second substrate separate from the first substrate. In this case, the two separate or otherwise discontinuous substrates represent two separate substrate pieces to be joined/bonded together in the article. In an alternative refinement, the first surface and the second surface are surfaces of a single substrate. In this case, the first and second surfaces can be two separate surfaces of a single substrate piece that curve or otherwise wrap around to be joined together. For example, a single flexible substrate with two surfaces at opposing end of the substrate each coated with the reversible adhesive composition can be used as an identifying wristband when wrapped around a user's wrist and reversibly joined at the two opposing surfaces.

In a refinement, the first surface and the second surface are formed from different materials, for example when the first and second surfaces are portions of separate substrates. In an alternative refinement, the first surface and the second surface are formed from the same material, for example when the first and second surfaces are portions of the same substrate or separate substrates.

The substrate or substrates in article are not particularly limited and can be formed from any material desired for reversible attachment to another surface or substrate. In a refinement, substrates in the article are independently selected from the group of metals and alloys, plastics, polymers, composites, glass, wood, fabric (or textile), paper substrate, organic-inorganic hybrid substrates, and ceramics. The plastics and polymers that can be used as substrates are generally different polymeric materials than the copolymer of the reversible adhesive composition. Examples of specific metals include steel, aluminum, copper, etc. Examples of specific plastics include polyvinyl alcohol (PVOH), ethylene vinyl alcohol (EVOH), polyethylene terephthalate (PET), polypropylene (PP), polyethylene (PE), polycarbonate (PC), acrylonitrile butadiene styrene (ABS), starch, chitosan, etc. Suitable wood materials can be any type of wood commonly used in home, office, and outdoor settings. Suitable glass materials can be those used for building windows, automobile windows, etc. In some embodiments, the substrate is a top layer of a coating or series of coatings on a different underlying substrate, and the reversible adhesive composition is applied to the top layer thereof.

While the disclosed compositions, articles, methods, and apparatus, are susceptible of embodiments in various forms, specific embodiments of the disclosure are illustrated (and will hereafter be described) with the understanding that the disclosure is intended to be illustrative, and is not intended to limit the claims to the specific embodiments described and illustrated herein.

BRIEF DESCRIPTION OF THE DRAWINGS

For a more complete understanding of the disclosure, reference should be made to the following detailed description and accompanying drawings wherein.

DETAILED DESCRIPTION

The disclosure relates to a reversible adhesive composition including a copolymer between a vinyl spacer monomer unit and a vinyl reversible binder monomer unit. Each monomer unit can be based on acrylate monomer, a vinyl ester monomer, or a vinyl ether monomer, with the spacer monomer unit generally having a shorter pendant chain (such as 1-3 carbon atoms) and the reversible binder monomer unit having a longer pendant chain (such as 3-20 carbon atoms). A corresponding article includes first and second surfaces (or substrates) that are in contact with and bonded to the reversible adhesive composition at an interface therebetween. The reversible adhesive composition generally involves non-covalent and/or non-ionic bonding forces, for example H-bonding, permanent dipole, electron donor-acceptor moieties, and/or van der Waals forces, between the copolymer chains. The first and second surfaces can be repeatedly bonded, separated, and re-bonded while retaining the adhesive strength of the reversible adhesive composition.

Reversibly Joined Article

Figure 10:
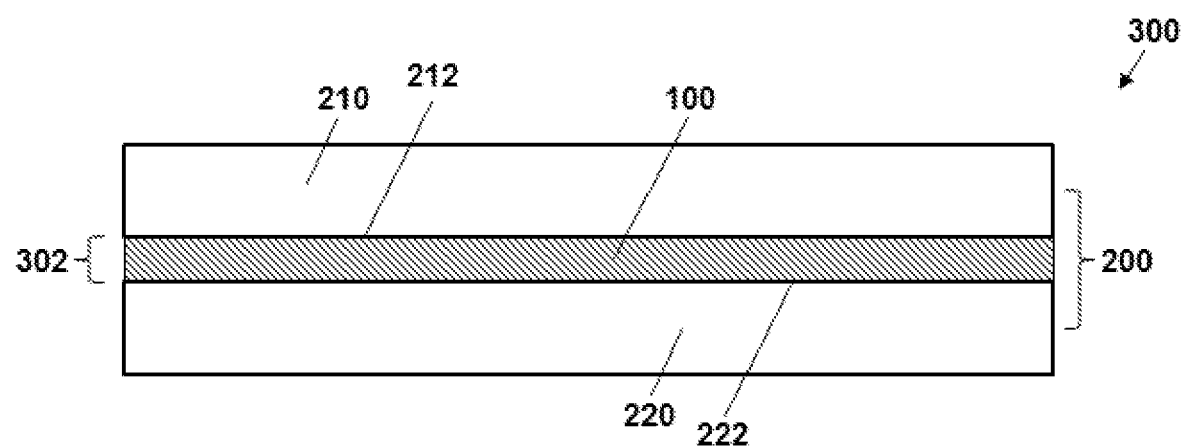
FIG. 10 illustrates an article including a reversible adhesive composition according to the disclosure.

FIG. 10 illustrates an aspect of the disclosure in which an article 300 includes two different surfaces 212, 222 joined at an interface 302 of the article 300. The surfaces 212, 222 can be a first surface 212 and a second surface 222, for example as exterior surfaces of a corresponding first substrate 210 and a corresponding second substrate 220, respectively. The surfaces 212, 222 are joined at the interface 302 by a reversible adhesive composition 100, which is in contact with and bonded to the surface 212, 222.

The article 300 is generally an assembled, multipart article 300 with reversibly joined surfaces 212, 222 using the reversible adhesive composition 100 in any of its disclosed embodiments. The first and second surfaces 212, 222 can be surfaces of the same or different substrate, and they are generally in an opposing orientation relative to each other, with the reversible adhesive composition 100 situated at the article interface 302 between the first and second surfaces 212, 222. The composition 100 can be in the form of a coating or film on either or both of the external, environment-facing surfaces 212, 222 of their corresponding (e.g., where the surface 202 would otherwise be exposed to the external environment in the absence of the composition 100). For example and as illustrated in FIG. 10, the first surface 212 can be an external surface of a first substrate 210 and the second surface 222 can be a surface of a second substrate 220 separate from the first substrate 210. In this case, the two separate or otherwise discontinuous substrates 210, 220 represent two separate substrate pieces to be joined/bonded together in the article 300. In some embodiments, the first surface 212 and the second surface 222 are surfaces of a single substrate 200. In this case, the first and second surfaces 212, 222 can be two separate surfaces of a single substrate 200 piece that curves or otherwise wraps around so that its surfaces cab be joined together. For example, a single flexible substrate 200 with two surfaces 212, 222 at opposing ends of the substrate 200 each coated with the reversible adhesive composition 100 can be used as an identifying wristband when wrapped around a user's wrist and reversibly joined at the two opposing surfaces 212, 222.

The substrate 200, substrates 210, 220, and their corresponding surfaces 212, 222 in the article 300 are not particularly limited and can be formed from any material desired for reversible attachment to another surface or substrate. In an embodiment, the first surface 212 and the second surface 222 are formed from different materials, for example when the first and second surfaces 212, 222 are portions of separate substrates 210, 220 that also are formed from different materials. In an alternative embodiment, the first surface 212 and the second surface 222 are formed from the same material, for example when the first and second surfaces 212, 222 are portions of the same substrate 200 or separate substrates 210, 222. Example materials for the substrates include metals and alloys, plastics, polymers, composites, glass, wood, fabric (or textile), paper substrate, organic-inorganic hybrid substrates, and ceramics. The plastics and polymers that can be used as substrates are generally different polymeric materials than the copolymer of the reversible adhesive composition. Examples of specific metals include steel, aluminum, copper, etc. Examples of specific plastics include polyvinyl alcohol (PVOH), ethylene vinyl alcohol (EVOH), polyethylene terephthalate (PET), polypropylene (PP), polyethylene (PE), polycarbonate (PC), acrylonitrile butadiene styrene (ABS), starch, chitosan, etc. Suitable wood materials can be any type of wood commonly used in home, office, and outdoor settings. Suitable glass materials can be those used for building windows, automobile windows, etc. In some embodiments, the substrate is a top layer of a coating or series of coatings on a different underlying substrate, and the reversible adhesive composition is applied to the top layer thereof.

The reversible adhesive composition 100 can have any desired thickness on the surfaces 212, 222. In common applications, the composition 100 has a thickness between the first surface and the second surface in a range from 0.005 µm to 5000 µm or 1 µm to 100 µm. In various embodiments, the thickness can be at least 0.005, 0.01, 0.1, 1, 2, 5, 10, 20, 50, or 100 µm and/or up to 10, 20, 50, 100, 200, 500, 1000, 2000, or 5000 The foregoing ranges similarly can apply to individual layers of the reversible adhesive composition on their respective surfaces before being joined/bonded together. The coatings can be cast, sprayed, spin-coated, etc., and multiple coatings can be applied to achieve any desired thickness.

The article can be formed by contacting the two initially separated surfaces 212, 222 each having at least a portion of the reversible adhesive composition 100 coated thereon. Contact can be effected by applying a suitable pressure for a sufficient time to bond the surfaces 212, 222 together at the interface 302 with the reversible adhesive composition 100 in the formed article 300. During a typical bonding or re-bonding step, the temperature is suitably greater than the glass transition temperature of the copolymer in the reversible adhesive composition. For example, the bonding or re-bonding step can be performed at approximately room temperature (e.g., about 20-30° C.) when such temperature is greater that the copolymer's glass transition temperature. Likewise, the bonding or re-bonding step can be performed with heating at an elevated temperature above room temperature when the glass transition temperature is also above room temperature, where the heating temperature is above the glass transition temperature. The surfaces 212, 222 and their corresponding substrates can be repeatedly de-bonded and/or re-bonded to disassemble and reassemble the article 300. Generally, a (pulling/separating) force is applied to one or both of the surfaces 212, 222 of the joined article 300 with a force sufficient to separate the surface 212, 222 while retaining at least a portion of the reversible adhesive composition 100 on each of the surfaces 212, 222. The surfaces 212, 222 can be rejoined as described above by contact a sufficient pressure and time to re-bond the two surfaces 212, 222.

Reversible Adhesive Composition

The reversible adhesive composition 100 can be used to reversibly join the first and second surfaces 212, 222 of one or more substrates as described above. The reversible binding capability of the adhesive composition permits repeated bonding and de-bonding at the interface 302 of the corresponding article 300 including the reversibly joined surfaces.

The reversible adhesive composition generally involves non-covalent and/or non-ionic bonding forces, for example H-bonding, permanent dipole, electron donor-acceptor moieties, and/or van der Waals forces, between the copolymer chains. Such forces act within the bulk of the reversible adhesive composition and between adjacent/touching reversible adhesive composition surfaces (e.g., when separate adhesive composition surfaces are contacted to form the article with joined surfaces). Such forces are generally stronger within the bulk of the composition and relatively weaker at the interface between adjacent/touching reversible adhesive composition surfaces, although the weaker forces at the interfacial locations are still sufficiently strong to bind the surfaces together. The relatively weaker forces at the interface allow the two surfaces to be repeatedly separated (with application of sufficient force) and re-joined at essentially the same location, thus leaving the reversible adhesive composition originally present on each surface essentially intact. There is no observed thread or fiber formation during the separation/de-bonding process.

Accordingly, even when the article is in assembled form, the reversible adhesive composition between the first and second surfaces can be itself characterized as having an internal interface between original portions/coatings of the reversible adhesive composition on each of the corresponding first and second surfaces. Such an internal interface within the reversible adhesive composition generally corresponds to the location where repeated bonding/de-bonding occurs. The reversible adhesive composition originally present on each surface can include the same or different copolymer relative to a corresponding surface to which it can be reversibly joined. When different reversible adhesive compositions/copolymers are used for complementary surfaces to be joined, one copolymer may have electron donating species and the other may have electron acceptor species to form a stronger reversible bond.

The reversible adhesive composition includes a copolymer with a vinyl spacer monomer unit (e.g., as a first monomer unit) and a vinyl reversible binder monomer unit (e.g., as a second monomer unit). The vinyl spacer monomer unit and the vinyl reversible binder monomer unit are different, in particular with respect to their corresponding pendent side chains. For example the vinyl reversible binder monomer unit generally has a longer pendant chain than the vinyl spacer monomer unit, such as being longer by at least 1, 2, 3, 4, 6, 8, or 10 carbon atoms and/or up to 4, 6, 8, 10, 14, or 18 carbon atoms.

As described in more detail below, the vinyl spacer monomer unit (e.g., and its corresponding monomer) can include a pendant carboxylate group with a carbonyl carbon backbone attachment and in the form of an acid, a salt, an ester with 1 to 3 carbon atoms in a corresponding ester group. Suitable salts include alkali metal salts such as with sodium or potassium. Suitable ester groups include linear or branched, substituted or unsubstituted methyl, ethyl, or propyl alkyl ester groups. Alternatively or additionally, the vinyl spacer monomer unit can include a pendant carboxylate group with an ester oxygen backbone attachment and having a hydrocarbon tail group with 1 to 3 carbon atoms. Alternatively or additionally, the vinyl spacer monomer unit can include a pendant ether group with an ether oxygen backbone attachment and having a hydrocarbon tail group with 1 to 3 carbon atoms. Suitable hydrocarbon tail groups for either the pendant carboxylate group or the pendant ether group include linear or branched, substituted or unsubstituted methyl, ethyl, or propyl alkyl tail groups.

As described in more detail below, the vinyl reversible binder monomer unit (e.g., and its corresponding monomer) can include a pendant carboxylate group with a carbonyl carbon backbone attachment and in the form of an ester having 3 to 20 carbon atoms in a corresponding ester group. Suitable ester groups include linear or branched, substituted or unsubstituted hydrocarbon groups such as alkyl groups. Alternatively or additionally, the vinyl reversible binder monomer unit can include a pendant carboxylate group with an ester oxygen backbone attachment and having a hydrocarbon tail group with 3 to 20 carbon atoms. Alternatively or additionally, the vinyl reversible binder monomer unit can include a pendant ether group with an ether oxygen backbone attachment and having a hydrocarbon tail group with 3 to 20 carbon atoms. Suitable hydrocarbon tail groups for either the pendant carboxylate group or the pendant ether group include linear or branched, substituted or unsubstituted hydrocarbon groups such as alkyl tail groups.

In an embodiment, the vinyl spacer monomer unit having a pendant carboxylate group with a carbonyl carbon backbone attachment can have a structure corresponding to a polymerization product (e.g., free radical or controlled radical polymerization or other suitable polymerization methods) of a vinyl spacer monomer according to formula I.A:

$$CH_2=CR'_1-C(=O)O-R'_2 \quad (I.A).$$

$R'_1$ is selected from hydrogen (H) and a methyl group. $R'_2$ is selected from hydrogen (H), an alkali metal (e.g., Na, K), and hydrocarbons containing from 1 to 3 carbon atoms. The hydrocarbons can be linear, branched, substituted, and/or unsubstituted, etc., for example including methyl, ethyl, propyl, or isopropyl groups and in particular having only 1 or 2 carbon atoms, optionally substituted with one or more N-, O-, P-, and/or S-containing functional groups. Selection of $R'_1$ as H corresponds to an acrylate/acrylic acid functional group. Selection of as $CH_3$ corresponds to a methacrylate/methacrylic acid functional group.

In an embodiment, the vinyl spacer monomer unit having a pendant carboxylate group with an ester oxygen backbone attachment can have a structure corresponding to a polymerization product (e.g., free radical or controlled radical polymerization or other suitable polymerization methods) of a vinyl spacer monomer according to formula II.A:

$$CH_2=CR'_3-OC(=O)-R'_4 \quad (II.A).$$

$R'_3$ is selected from hydrogen (H) and a methyl group. $R'_4$ is selected from hydrocarbons containing from 1 to 3 carbon atoms. The hydrocarbons can be linear, branched, substituted, and/or unsubstituted, etc., for example including methyl, ethyl, propyl, or isopropyl groups and in particular having only 1 or 2 carbon atoms, optionally substituted with one or more N-, O-, P-, and/or S-containing functional groups. The monomer according to formula II.A generally corresponds to a vinyl ester monomer, for example vinyl acetate or longer-chain and/or substituted analogs thereof.

In an embodiment, the vinyl spacer monomer unit having a pendant ether group with an ether oxygen backbone attachment can have a structure corresponding to a polymerization product (e.g., free radical or controlled radical polymerization or other suitable polymerization methods) of a vinyl spacer monomer according to formula III.A:

$$CH_2=CR'_5-O-R'_6 \quad (III.A).$$

$R'_5$ is selected from hydrogen (H) and a methyl group. $R'_6$ is selected from hydrocarbons containing from 1 to 3 carbon atoms. The hydrocarbons can be linear, branched, substituted, and/or unsubstituted, etc., for example including methyl, ethyl, propyl, or ispropyl groups and in particular having only 1 or 2 carbon atoms, optionally substituted with one or more N-, O-, P-, and/or S-containing functional groups. The monomer according to formula III.A generally corresponds to a vinyl ether monomer, for example vinyl methyl ether or longer-chain and/or substituted analogs thereof.

In an embodiment, the vinyl reversible binder monomer having a pendant carboxylate group with a carbonyl carbon backbone attachment can have a structure corresponding to a polymerization product (e.g., free radical or controlled radical polymerization or other suitable polymerization methods) of a vinyl reversible binder monomer according to formula I.B:

$CH_2=CR_1—C(=O)O—R_2$ (I.B).

$R_1$ is selected from hydrogen (H) and a methyl group. $R_2$ is selected from hydrocarbons containing from 3 to 20 carbon atoms. The hydrocarbons can be linear, branched, substituted, unsubstituted, cyclic, aliphatic, or aromatic, saturated, and/or unsaturated, etc., for example having at least 3, 4, 5, 6, 8, 10, or 12 and/or up to 8, 10, 12, 14, 16, 18, or 20 carbon atoms, optionally substituted with one or more N-, O-, P-, and/or S-containing functional groups or atoms. Example functional groups present in $R_2$ can include one or more of halogen atoms, alkyl groups (e.g., as a chain or a terminal $CH_3$ group, such as at the end of a chain or a branch), aryl groups, hydroxyl groups, amine groups, nitrile groups, ester groups, carboxylic acid groups, aldehyde groups, ketone groups, ether groups, and combinations thereof. Selection of $R_1$ as H corresponds to an acrylate/acrylic acid functional group. Selection of $R_1$ as $CH_3$ corresponds to a methacrylate/methacrylic acid functional group.

In an embodiment, the vinyl reversible binder monomer having a pendant carboxylate group with an ester oxygen backbone attachment can have a structure corresponding to a polymerization product (e.g., free radical or controlled radical polymerization or other suitable polymerization methods) of a vinyl reversible binder monomer according to formula II.B:

$CH_2=CR_3—OC(=O)—R_4$ (II.B).

$R_3$ is selected from hydrogen (H) and a methyl group. $R_4$ is selected from hydrocarbons containing from 3 to 20 carbon atoms. The hydrocarbons can be linear, branched, substituted, unsubstituted, cyclic, aliphatic, or aromatic, saturated, and/or unsaturated, etc., for example having at least 3, 4, 5, 6, 8, 10, or 12 and/or up to 8, 10, 12, 14, 16, 18, or 20 carbon atoms, optionally substituted with one or more N-, O-, P-, and/or S-containing functional groups or atoms. Example functional groups present in $R_4$ can include one or more of halogen atoms, alkyl groups (e.g., as a chain or a terminal $CH_3$ group, such as at the end of a chain or a branch), aryl groups, hydroxyl groups, amine groups, nitrile groups, ester groups, carboxylic acid groups, aldehyde groups, ketone groups, ether groups, and combinations thereof. The monomer according to formula II.B generally corresponds to a vinyl ester monomer, for example vinyl butyrate or longer-chain and/or substituted analogs thereof.

In an embodiment, the vinyl reversible binder monomer having a pendant ether group with an ether oxygen backbone attachment can have a structure corresponding to polymerization product (e.g., free radical or controlled radical polymerization or other suitable polymerization methods) of a vinyl reversible binder monomer according to formula III.B (e.g., pendant ether group with an ether oxygen backbone attachment):

$CH_2=CR_5—O—R_6$ (III.B).

$R_5$ is selected from hydrogen (H) and a methyl group. $R_6$ is selected from hydrocarbons containing from 3 to 20 carbon atoms. The hydrocarbons can be linear, branched, substituted, unsubstituted, cyclic, aliphatic, or aromatic, saturated, and/or unsaturated, etc., for example having at least 3, 4, 5, 6, 8, 10, or 12 and/or up to 8, 10, 12, 14, 16, 18, or 20 carbon atoms, optionally substituted with one or more N-, O-, P-, and/or S-containing functional groups or atoms. Example functional groups present in $R_6$ can include one or more of halogen atoms, alkyl groups (e.g., as a chain or a terminal $CH_3$ group, such as at the end of a chain or a branch), aryl groups, hydroxyl groups, amine groups, nitrile groups, ester groups, carboxylic acid groups, aldehyde groups, ketone groups, ether groups, and combinations thereof. The monomer according to formula III.B generally corresponds to a vinyl ether monomer, for example vinyl butyl ether or longer-chain and/or substituted analogs thereof.

More than one type of vinyl spacer monomer unit can be included and/or more than one type of vinyl reversible binder monomer unit can be included in the copolymer. For example, more than one type of vinyl spacer monomer according to any of formulas I.A, II.A, or III.A can be used. Similarly, more than one type of vinyl reversible binder monomer according to any of formulas I.B, II.B, or III.B can be used. When one monomer is an acrylate-based monomer and another monomer is a vinyl ester- or vinyl-ether based monomer, the resulting copolymer can include alternating segments. When both monomers are acrylate-based monomers, or both monomers vinyl ester- or vinyl-ether based monomers, the resulting copolymer can include statistical/random segments. Suitably, at least one monomer includes a pendant methyl group, which is useful to control the glass transition temperature of the copolymer to be within a desired range for a reversible adhesive. This can suitably be the case when the methyl group is incorporated into the spacer monomer unit, such as when $R'_1$, $R'_3$, or $R'_5$ is methyl in formula I.A, II.A, or III.A, respectively. In such cases, $R_1$, $R_3$, or $R_5$ can be hydrogen in formula I.B, II.B, or III.B, respectively. Alternatively, the methyl group can be incorporated into the binder monomer unit, with the analogous positions on the spacer monomer unit being hydrogen.

The vinyl spacer monomer units and vinyl reversible binder monomer units can be included in the corresponding copolymer in any suitable relative amounts that provide desired physical and chemical properties while still permitting reversible bonding at an interface. For example the vinyl spacer monomer units can be present in the copolymer in a range from 10 mol. % to 90 mol. % relative to total vinyl spacer monomer units and vinyl reversible binder monomer units combined. Similarly, the vinyl reversible binder monomer units can be present in the copolymer in a range from 10 mol. % to 90 mol. % relative to total vinyl spacer monomer units and vinyl reversible binder monomer units combined. More generally, the vinyl spacer monomer units can be present in an amount of at least 10, 20, 30, 40, 45, 50, 55, 60, or 70 mol. % and/or up to 40, 45, 50, 55, 60, 70, 80, or 90 mol. %. Likewise, the vinyl reversible binder monomer units can be present in an amount of at least 10, 20, 30, 40, 45, 50, 55, 60, or 70 mol. % and/or up to 40, 45, 50, 55, 60, 70, 80, or 90 mol. %. Suitably, at least 50, 60, 70, 80, 90, or 95 mol. % and/or up to 70, 80, 90, 95, or 98 mol. % of the copolymer corresponds to total vinyl spacer monomer units and vinyl reversible binder monomer units. Similar ranges can apply on a weight basis for the respective monomer units.

In an embodiment refinement, the copolymer can include a third (or subsequent) monomer unit, for example a vinyl crosslinking monomer unit. The vinyl crosslinking monomer unit can provide crosslinks between copolymer chains via the vinyl crosslinking monomer unit. The third monomer unit or vinyl crosslinking monomer unit can be incorporated into the copolymer in an amount from 0.5 mol. % to 20 mol.

%, for example at least 0.5, 1, 2, 3, 4, 5, or 8 mol. % and/or up to 4, 6, 8, 10, 12, 16, or 20 mol. %, for example based on (i) total vinyl spacer monomer units and vinyl reversible binder monomer units combined or (ii) total vinyl monomer units combined.

The vinyl crosslinking monomer unit can be derived from a vinyl monomer with a pendant hydroxyl group or amine group, for example for crosslinking with a diisocyanate, triisocyanate, or other polyisocyanate, thus imparting urethane or urea crosslinks into the copolymer. Examples of suitable vinyl crosslinking monomers include 2-hydroxyethyl (meth)acrylate, 2-aminoethyl (meth)acrylate, etc. In some embodiments, the pendant amine or hydroxyl group(s) can be selected to form reversible urea or reversible urethane crosslinks in the copolymer. Examples of amine groups capable of forming a reversible urea bond with an isocyanate include hindered secondary amino groups, such as in a vinyl monomer including at least one, two, or more hindered secondary amino groups. Examples of hydroxy groups capable of forming a reversible urethane bond with an isocyanate include aromatic hydroxy groups, such as in a vinyl monomer including at least one, two, or more aromatic hydroxy groups. Examples of suitable hindered secondary amino groups and aromatic hydroxy groups as well as corresponding reversible urea or reversible urethane bonds may be found in WO 2020/142578, which is incorporated herein by reference. An example of a vinyl crosslinking monomer including a hindered amino group capable of forming a reversible urea bond with an isocyanate includes tert-butylamine propyl acrylate, for example in a reversible adhesive copolymer such as poly(methyl acrylate-random-alkyl acrylate-random-3-tert-butylamine propyl acrylate) (p(MA-ran-AA-ran-tBAPA)). When the 3-tert-butylamine units (or other hindered amino groups) react with polyisocyanates, they can form a crosslinked structure via reversible covalent urea bonds. The resultant dynamic crosslinking can impart high cohesive and adhesive strengths, while the reversibility will be retained due to the reversible nature of the selected urea bond at room temperature. The presence of dynamic/reversible urea bonds or urethane bonds in the reversible adhesive copolymer can permit covalent bond formation at interfaces when samples of the adhesive that are affixed to two different surfaces are brought together. The reversible adhesive interactions between the primary vinyl spacer monomer units and vinyl reversible binder monomer units can provide multiple functions. First, they offer initial adhesion between the two substrates. Second, this initial adhesion will allow the dynamic urea or urethane groups to come close to each other at a molecular level to facilitate the interchange between these groups. This can form covalent bonds at the interface between the two newly joined substrates. Consequently, the simultaneous presence of van der Waals and dynamic covalent bonds can not only enhance the adhesive strength at the interface but can also increase the cohesive strength because the dynamic bonds act as cross-linked points.

Suitable polyisocyanates can include any aromatic, alicyclic, and/or aliphatic isocyanates having at least two (e.g., 2-4) reactive isocyanate groups (—NCO). Examples of specific polyisocyanates include 1,5-naphthylene diisocyanate, 4,4'-diphenylmethane diisocyanate (MDI), hydrogenated MDI, xylene diisocyanate (XDI), tetramethylxylol diisocyanate (TMXDI), 4,4'-diphenyl-dimethylmethane diisocyanate, di- and tetraalkyl-diphenylmethane diisocyanate, 4,4'-dibenzyl diisocyanate, 1,3-phenylene diisocyanate, 1,4-phenylene diisocyanate, one or more isomers of tolylene diisocyanate (TDI, such as toluene 2,4-diisocyanate), 1-methyl-2,4-diiso-cyanatocyclohexane, 1,6-diisocyanato-2,2,4-trimethyl-hexane, 1,6-diisocyanato-2,4,4-trimethylhexane, 1-iso-cyanatomethyl-3-isocyanato-1,5,5-trimethyl-cyclohexane, chlorinated and brominated diisocyanates, phosphorus-containing diisocyanates, 4,4'-diisocyanatophenyl-perfluoroethane, tetramethoxybutane 1,4-diisocyanate, butane 1,4-diisocyanate, hexane 1,6-diisocyanate (or hexamethylene diisocyanate; HDI), HDI dimer (HDID), HDI trimer (HDIT), HDI biuret, 1,5-pentamethylene diisocyanate (PDI), PDID (dimer of PDI), PDIT (trimer of PDI), PDI biuret, dicyclohexylmethane diisocyanate, cyclohexane 1,4-diisocyanate, ethylene diisocyanate, phthalic acid bisisocyanatoethyl ester, 1-chloromethylphenyl 2,4-diisocyanate, 1-bromomethylphenyl 2,6-diisocyanate, 3,3-bischloromethyl ether 4,4'-diphenyldiisocyanate, trimethylhexamethylene diisocyanate, 1,4-diisocyanato-butane, 1,2-diisocyanatododecane, and combinations thereof.

In an embodiment, the copolymer of the reversible adhesive composition includes statistical segments with the vinyl spacer monomer units and the vinyl reversible binder monomer unit. The copolymer can include statistical or random copolymer segments (e.g., ABAABBBAABAABB), for example when the spacer and reversible binder are based on acrylate monomers. The copolymer can be formed substantially entirely as a statistical or random copolymer. In some embodiments, only a portion of the copolymer includes the spacer and reversible binder units, for example when the copolymer includes (block) portions of the copolymer that could be non-binding (e.g., formed from spacer units or otherwise) joined by segments of statistical/random spacer/reversible binder units. Non-binding portions of the copolymer can be 0-90 mol. % or wt. %, for example about 5 or 10 to 30 or 40 mol. % or wt. %. In some embodiments, a single copolymer can include some blocks having one kind of binding interactions (e.g., van der Waals) and some blocks having another kind of binding interactions (e.g. dipole moment).

In an embodiment, the copolymer of the reversible adhesive composition includes alternating segments between the vinyl spacer monomer units and the vinyl reversible binder monomer unit. The copolymer can include alternating copolymer segments (e.g., ABABABABAB), for example when the spacer is based on an acrylate monomer and the reversible binder is based on a non-acrylate monomer such as vinyl ether or vinyl ester. The copolymer can be formed substantially entirely as an alternating copolymer. The alternating structure generally has a 1:1 molar ratio between the two alternating units in the copolymer, although the ratio of monomers in the reactant/feed can vary. Similar to above, in some embodiments, only a portion of the copolymer includes the spacer and reversible binder units, for example when the copolymer includes (block) portions of the copolymer that could be non-binding (e.g., formed from spacer units or otherwise) joined by segments of alternating 1:1 spacer/reversible binder units. Non-binding portions of the copolymer can be 0-90 mol. % or wt. %, for example about 5 or 10 to 30 or 40 mol. % or wt. %. Such structures can be formed using a semi-batch synthesis or selective polymerization in the presence of more than 2 monomers.

The copolymer of the reversible adhesive composition suitably has a glass transition temperature in a range from $-10°$ C. to $18°$ C. More generally, the copolymer can have a glass transition temperature of at least $-20°$ C., $-10°$ C., $0°$ C., $10°$ C., $20°$ C., $30°$ C. or $40°$ C. and/or up to $10°$ C., $18°$ C., $20°$ C., $40°$ C., $60°$ C., or $80°$ C. When the reversible adhesive composition is intended to be used (e.g., bonded and/or de-bonded) at ambient temperature conditions (e.g., about 20-25° C.), the glass transition temperature can be in a range from −20° C. to 10° C. or −10° C. to 18° C. such that ambient heat in combination with mild applied pressure is typically sufficient to effect bonding. In embodiments where the glass transition temperature is above ambient temperature conditions, the glass transition temperature can be in a range from 30° C. to 80° C. or 40° C. to 60° C. such that applied heat would be used in combination with pressure to effect bonding. Alternatively or additionally, the copolymer can have a molecular weight in a range from 1,500 g/mol to 2,000,000 g/mol or 25,000 g/mol to 200,000 g/mol. In various embodiments, the molecular weight can be at least 1,500, 5,000, 10,000, 25,000, or 50,000 and/or up to 50,000, 100,000, 200,000, 500,000, or 2,000,000 g/mol. The molecular weight can be expressed as a number-average or weight-average value in the units of gram/mole (g/mol).

In an embodiment and due to the reversible binding ability of the reversible adhesive composition 100, the first surface 212 and the second surface 222 are capable of being separated from each other without damage to the surfaces 212, 222, while at least a portion of the reversible adhesive composition 100 remains each of the surfaces 212, 222. The separated surfaces 212, 222 are then capable of being rejoined at the interface 302 with the reversible adhesive composition 100 in contact with and bonded to the surfaces 212, 222. The joined surfaces can be separated with application of a non-destructive level of force/stress, for example to pull them apart. The separated surfaces can subsequently be rejoined by re-contacting the surfaces at the interface with the reversible adhesive composition there between, for example with application of minor pressure. Specifically, the first and second surfaces (or their corresponding substrates) can be each initially provided with an external film, coating, discrete dot, or other layer of the reversible adhesive composition, and reversible bonding occurs when two opposing copolymer-copolymer surfaces of respective opposing films, coatings, dots, or other layers are contacted. The layer of the reversible adhesive composition can be initially provided its corresponding surface or substrate by any suitable method such as solvent casting, hot-melt application, water-borne formulation application, powder-melt application, etc.

The joined surfaces can be repeatedly separated and re-joined without substantially reducing the strength of the interface bonding the two surfaces. For example, the interface bonding/joining the two surfaces can have a yield strength of at least 80% (e.g., at least 80, 85, 90, or 95% and/or up to 90, 95, 98, or 99%) relative to initial yield strength after 5, 10, 20, 50, or 100 cycles of separation/rejoining, where the yield strength corresponds to the minimum load required to separate joined surfaces, and the initial yield strength is the yield strength after the first joining of the surfaces. The absolute yield strength for typical joined surfaces is not particularly limited, but it can range from about 0.01 MPa to 500 MPa (e.g., at least 0.01, 0.1, 0.5, 1, 2, 5, or 10 MPa and/or up to 5, 10, 20, 50, 100, 200, to 500 MPa). The pressure required to (re)bond separated surfaces/substrates is not particularly limited, but it can range from about 0.1 N to 400 N (e.g., at least 0.1, 0.5, 1, 2, 5, 10, 20, 30, 40, or 50 N and/or up to 20, 40, 60, 80, 100, 200, or 400 N). The contact time for applied pressure to (re)bond is not particularly limited, but it can range from about 2 sec to 600 sec (e.g., at least 2, 5, 10, 20, or 30 sec and/or up to 30, 60, 120, 240, or 600 sec).

The reversible adhesive composition can include one or more additives. The additives can be present in admixture with the copolymer of the reversible adhesive composition, but they are generally not (covalently) bonded thereto. In some embodiments, the additives can be in solid form when combined with the copolymer of the reversible adhesive composition. In other embodiments, reactive components corresponding to the additive can be combined with monomer components corresponding to the reversible adhesive copolymer (e.g., vinyl spacer monomers and vinyl reversible binder monomers), and the additive can be formed in situ with the reversible adhesive copolymer, but as a separate component relative to the reversible adhesive copolymer. Examples of additives can include silica, poly(methylmethacrylate) (PMMA), an epoxy resin (e.g., a thermoset), and polystyrene, for example in the form of particles distributed throughout the reversible adhesive composition. The additives can be particularly useful for a variety of applications, for example as a physical crosslinker improving adhesiveness of the composition, improving use in high-temperature applications, and/or improving adhesion to substrates different in chemical nature than the adhesives. For example, in a blend of polystyrene and poly(methylmethacrylate-co-n-butylacrylate) (p(MMA/nBA)), the domains of the polystyrene do not soften until about 100° C., while the p(MMA/nBA) softens at about 40° C. and thus the polystyrene additive function as physical crosslinking agent. In addition, the use of polystyrene in the (p(MMA/nBA)) will enhance adhesion with polystyrene films as polystyrene (e.g., in substrate/film) and polystyrene (e.g., in the adhesive mixture) have an affinity for each other. Similarly, other polymers can be added to increase adhesion with other substrates. Silica can be used because of its structural rigidity, spherical morphology, low cost, and ability to enhance the toughness of many organic polymers. In certain cases, compatibalizers can be used with physical crosslinking agents are added to reduce phase separation between the crosslinking agents and the reversible adhesive matrix.

As described above, epoxy compounds can be used as additives with the reversible adhesive composition. An epoxy compound can be a useful additive because their epoxide-functional monomer and amino-functional hardener react to form rigid polymers (e.g., a crosslinked epoxy thermoset). For example, when epoxide and amine monomers are mixed to react in another polymer or monomer mixture (e.g., vinyl spacer monomers and vinyl reversible binder monomers for formation of the reversible adhesive copolymer), then polymerization-induced phase separation can occur where the hard epoxy reaction product can form as particles dispersed in a viscoelastic reversible adhesive copolymer matrix (e.g., p(MMA/nBA) or otherwise). Suitably, the dispersed epoxy phase occupies less than 25 vol. % of the mixture, for example with the epoxy phase dispersed as hard spheres in the continuous matrix.

As described above, poly(methylmethacrylate) (PMMA) also can be used as an additives with the reversible adhesive composition. PMMA can be a useful additive or filler because PMMA is a rigid material (e.g., having a high glass transition temperature Tg). PMMA can act as a physical crosslinker while also having a greater affinity towards the reversible adhesive copolymer, for example a p(MMA/nBA) reversible adhesive copolymer because of the similarity of their chemical structures (e.g., a shared acrylate structure between MMA and nBA). More generally, other rigid polymers can be used as an additive and provide physical crosslinking functionality, for example when the additive polymer has some chemical similarity with the reversible adhesive copolymer, such as a same or similar monomer unit between the two polymers.

EXAMPLES

The following examples illustrate the disclosed compositions and methods, but are not intended to limit the scope of any claims thereto. The following examples provide illustrative reversible adhesive compositions and corresponding articles according to the disclosure. The adhesives and corresponding reversibly joined articles were tested for various mechanical properties to evaluate adhesion or bond strength.

Example 1—Poly(PMMA/nBA) Reversible Adhesive

The example illustrates a reversible adhesive including various poly methyl methacrylate-co-poly butyl acrylate (PMMA/nBA) copolymers according to the disclosure as well as articles including reversibly joined surfaces or substrates using the reversible adhesives.

Materials:

The monomers and reagents such as methyl methacrylate (MMA), n-butyl acrylate (nBA), and 2,2'-Azobis(2methyl-propionitrile) (AIBN) were purchased from Sigma-Aldrich. The solvents used in synthesis and precipitations were HPLC grade toluene and hexane which were also purchased from Sigma Aldrich. Similarly, activated neutral alumina from Sigma Aldrich was used to purify MMA and nBA prior to polymerization. Wood blocks as test substrates for joining were purchased from local Home Depot.

Figure 1:
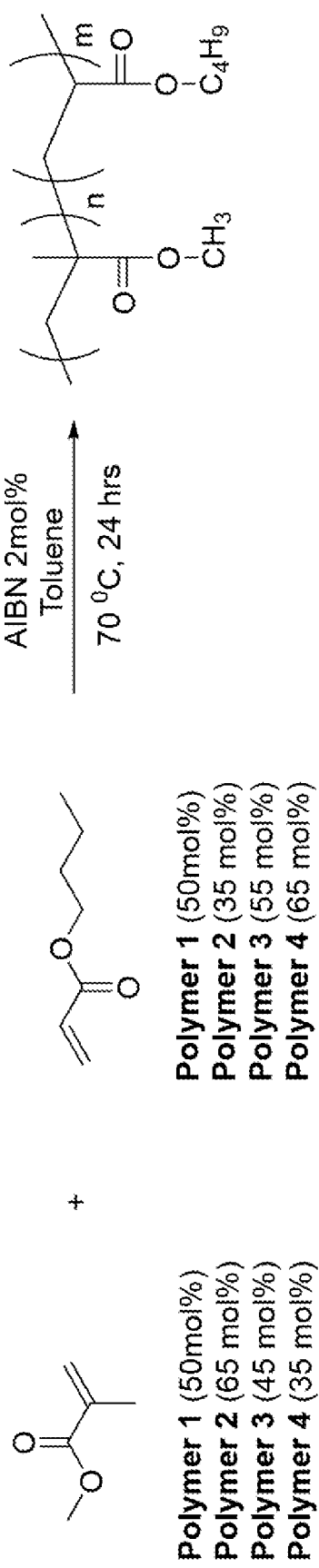
FIG. 1 is a reaction scheme illustrating the synthesis and composition of reversible adhesive copolymers according to the disclosure.

Procedure:

Four polymers 1, 2, 3 and 4 as shown in FIG. 1 were synthesized as follows. Stabilizer-free MMA and n-nBA were degassed by applying a freeze-pump-thaw method and were transferred into a glove box. Various feed-ratios of the monomers (MMA: nBA) (i.e., 50 mol %:50 mol %; 65 mol %:35 mol %; 45 mol %:55 mol %; and gh) were added into separate reaction flasks inside the glove box. Degassed toluene was added as diluent/solvent along 2.0 mol % AIBN as a free radical initiator. All the reactions were stirred at 70° C. for 24 hrs before being quenched via exposure to open air at ambient temperature. A small fraction of each crude reaction mixtures was characterized by $^1$H NMR to obtain the degree of conversion for each monomer. The remaining crude mixture was precipitated from hexane for three times, and the obtained precipitates were subsequently dried in a vacuum oven at 40° C. overnight prior to further processing and characterization.

The polymers were characterized via $^1$H NMR, GPC analysis, DSC, TGA and DMA. $^1$H NMR analysis were conducted on a 500 MHz NMR spectrometer (Agilent, Santa Clara, Calif., USA) using CDCl$_3$ as the solvent. For the molecular weight determination via GPC, an amount of about 10 mg of each polymer was dissolved in 1 mL of GPC-grade tetrahydrofuran (THF), which was then filtered through a micro filter fitted on a 1 mL syringe. The samples were run on a water GPC instrument working with tetrahydrofuran as the solvent and pre-calibrated with GPC-grade polystyrene standards. The molecular weights for each polymer were then calculated using the refractive index (RI) detector. The thermogravimetric analysis (TGA), differential scanning calorimetry (DSC), and dynamic mechanical analysis (DMA) were carried out using TA instruments, Q50 model, Q100 model, and RSA-G2 model, respectively. Both TGA and DSC analyses were performed under inert conditions at rate of 100° C./min change in temperature, while the viscoelastic properties using DMA were evaluated at ambient conditions within the linear viscoelastic region (LVE).

Synthesis of Polymer 1:

Polymer 1 (poly Methyl methacrylate-co-poly butyl acrylate or PMMA/nBA, 50/50) was synthesized by adding 32.10 mL (0.299 mol) of purified and degassed methyl methacrylate and 42.90 mL (0.299 mol) of n-butyl acrylate into a 300 mL slink flask. To the flask was then added 15 mL of degassed toluene, and the mixture was stirred at ambient temperature for 5 min. After a complete mixing of the monomers, 1.97 g (2 mol %) of AIBN was added to the flask. The flask was then sealed with a septum and stirred under heating at 70° C. for 24 hrs. The crude mixture after >90% of the monomers had polymerized was quenched by exposing to room temperature. The reaction mixture was precipitated from hexane, and the precipitate was then dried under vacuum at 40° C. for 10 hrs. Polymer 1 was characterized by HNMR and GPC analysis: $^1$HNMR (300 MHz, CDCl$_3$) δ (ppm): 3.94 (nBA-OCH$_2$—, 3.58 (MMA-OCH$_3$—), 0.784-2.05 (MMA-CH$_3$—, nBA-CH$_3$—, nBA-CH$_2$—, back bone-CH$_2$—, back bone-CH—). GPC; =38469 g·mol$^{-1}$, M$_n$=88024 g·mol$^{-1}$, PDI=2.28.

Synthesis of Polymer 2:

Polymer 2 (poly Methyl methacrylate-co-poly butyl acrylate or PMMA/nBA, 65/35) was synthesized similarly to polymer 1, but using 32.10 mL (0.299 mol) of methyl methacrylate, 23.14 mL (0.162 mol) of n-butyl acrylate, and 1.512 g (2 mol %) of AIBN. Polymer 2 was characterized by HNMR and GPC analysis: $^1$HNMR (300 MHz, CDCl$_3$) δ (ppm): 3.96 (nBA-OCH$_2$—, 3.53 (MMA-OCH$_3$—), 0.784-2.02 (MMA-CH$_3$—, nBA-CH$_3$—, nBA-CH$_2$—, back bone-CH$_2$—, back bone-CH—). GPC; =9911 g·mol$^{-1}$, M$_n$=24825 g·mol$^{-1}$, PDI=2.51.

Synthesis of Polymer 3:

Polymer 3 (poly Methyl methacrylate-co-poly butyl acrylate or PMMA/nBA, 45/55) was synthesized similarly to polymer 1, but using 32.10 mL (0.299 mol) of methyl methacrylate, 52.5 mL (0.366 mol) of n-butyl acrylate, and 2.19 g (2 mol %) of AIBN. Polymer 3 was characterized by HNMR and GPC analysis: $^1$HNMR (300 MHz, CDCl$_3$) δ (ppm): 3.94 (nBA-OCH$_2$—, 3.53 (MMA-OCH$_3$—), 0.784-2.02 (MMA-CH$_3$—, nBA-CH$_3$—, nBA-CH$_2$—, back bone-CH$_2$—, back bone-CH—). GPC; =38553 g·mol$^{-1}$, M$_n$=78063 g·mol$^{-1}$, PDI=2.02.

Synthesis of Polymer 4:

Polymer 4 (poly Methyl methacrylate-co-poly butyl acrylate or PMMA/nBA, 35/65) was synthesized similarly to polymer 1, but using 32.10 mL (0.299 mol) of methyl methacrylate, 79.08 mL (0.551 mol) of n-butyl acrylate, and 2.19 g (2 mol %) of AIBN. Polymer 4 was characterized by HNMR and GPC analysis: $^1$HNMR (300 MHz, CDCl$_3$) δ (ppm): 3.93 (nBA-OCH$_2$—, 3.51 (MMA-OCH$_3$—), 0.77-2.00 (MMA-CH$_3$—, nBA-CH$_3$—, nBA-CH$_2$—, back bone-CH$_2$—, back bone-CH—); GPC; M$_n$=46902 g·mol$^{-1}$, M$_w$=114795 g·mol$^{-1}$, PDI=2.45.

Tensile Strength Analysis for Polymers and Articles:

In order to determine the tensile strength of the polymers, each polymer (about 10 grams) was dissolved in 10 mL of dichloromethane and was poured into the custom made poly(tetrafluoroethylene) (PTFE) trays, where slow evaporation of the dichloromethane produced transparent films of the dissolved polymers. The films were completely dried in 24 hrs at ambient temperature and were then peeled off from the PTFE trays. The resulting films were cut into tensile film specimens, which were then tested with an Instron tensile testing machine at a cross-head speed of 1.5 in/min and a load cell with maximum capacity of 500N. For each polymer, at least five samples were run to determine the polymer's load-deformation curve (i.e., force vs. extension) and averaged stress-strain curves.

The formulated polymers of this example were used as adhesives to manufacture wooden butt joints to investigate the adhesive strength of the polymers as polyacrylate-based glues for joints and construction purposes. An amount of 5 g of each polymer mixture was dissolved in 5 mL of dichloromethane and the obtained viscous solution was casted on the wood surface. The evaporation of dichloromethane resulted in the formation of adhesive layer on the wood. The wooden adherents were then bonded by pressing together for controlled times and loads, including 15 lbs (67N), 30 lbs (134N), and 60 lbs (267N). Butt joint samples were tested on an Instron tensile testing machine according to ASTM D2095-96 to determine the force-displacement curve from, the calculated force (N) at failure, and displacement (mm) at failure for the tested butt joints. The dwell time for all three loads on all adhered samples was 2 minutes. After 2 minutes of squeezing under varying loads, the adhered samples were set for different time intervals of 10 mins, 2 hrs and 10 hrs, to evaluate the effect of time on adhesive strengths.

The reversibility of the polymer adhesives was also examined. The butt joint test was repeatedly carried for various specimens with each polymer. For the peel repeatability test, the 15 lbs (67N) load for 2 mins (press time) and 10 minutes (set time) were selected. The reversibility/repeatability for the adhesive strength was similarly tested on the Instron tensile testing machine to measure force-displacement curves and the calculated force at failure.

Figure 2:
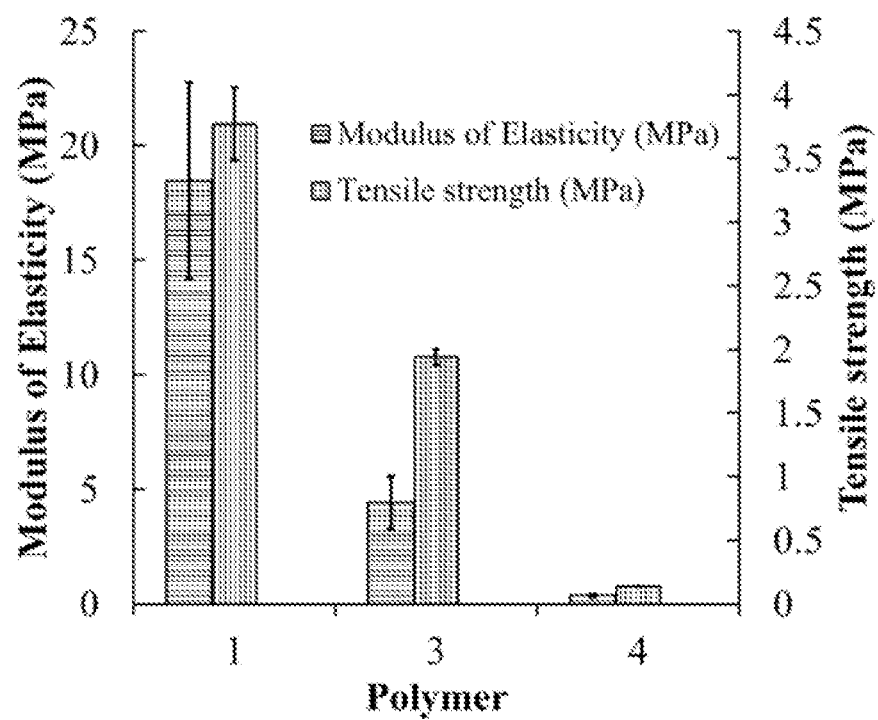
FIG. 2 is a graph showing the variation of modulus of elasticity and tensile strength for reversible adhesive copolymers according to the disclosure.

Polymer Tensile Testing:

The modulus of elasticity (MOE), strain to failure, and tensile strength of the adhesives were evaluated using macroscopic tensile testing. Only three out of four polymer adhesives (polymers 1, 3 and 4) were evaluated for their tensile properties. The tensile properties for polymer 2 were not evaluated due to its brittle nature, which gave very fragile films unable to be cut into samples for tensile testing. The brittle nature of the polymer 2 is attributed to its high PMMA content (65 mol. %). The variation of MOE (FIG. 2), tensile strength (FIG. 2) and strain to failure (FIG. 3) were recorded for polymer 1, 3, and 4. While MOE and tensile strength reduced, the strain to failure increased as the MMA/nBA ratio decreased. As MMA/nBA ratio was reduced from 50/50 (polymer 1) to 45/55 (polymer 3), the MOE and tensile strength was dropped by ~76% and ~48% respectively. Further reduction of MMA/nBA ratio to 35/65 (polymer 4) resulted in ~91% drop in MOE and ~93% drop in tensile strength. Unlike MOE and tensile strength, the strain to failure increased as the MMA/nBA ratio decreased. The strain to failure was approximately 3 times higher for polymer 4 (MMA/nBA (35/65) when compared to polymer 1 and 2. Although MOE and tensile strength are important parameters in determining the adhesive characteristics, adhesive toughness as reflected by strain to failure is also an important factor in increasing the shear strength of bonded joints. Accordingly, adhesives can be prepared with a tailored set of tensile properties by adjusting the relative ratio of monomer components (e.g., MMA and nBA in this example).

Figure 3:
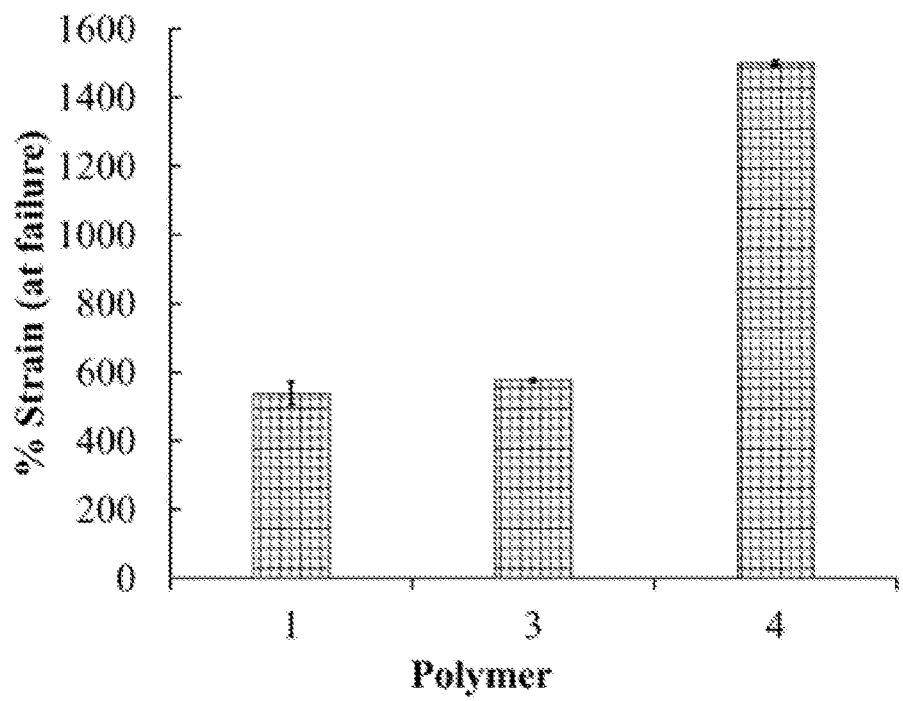
FIG. 3 is a graph showing the variation of strain to failure for reversible adhesive copolymers according to the disclosure.
Figure 4:
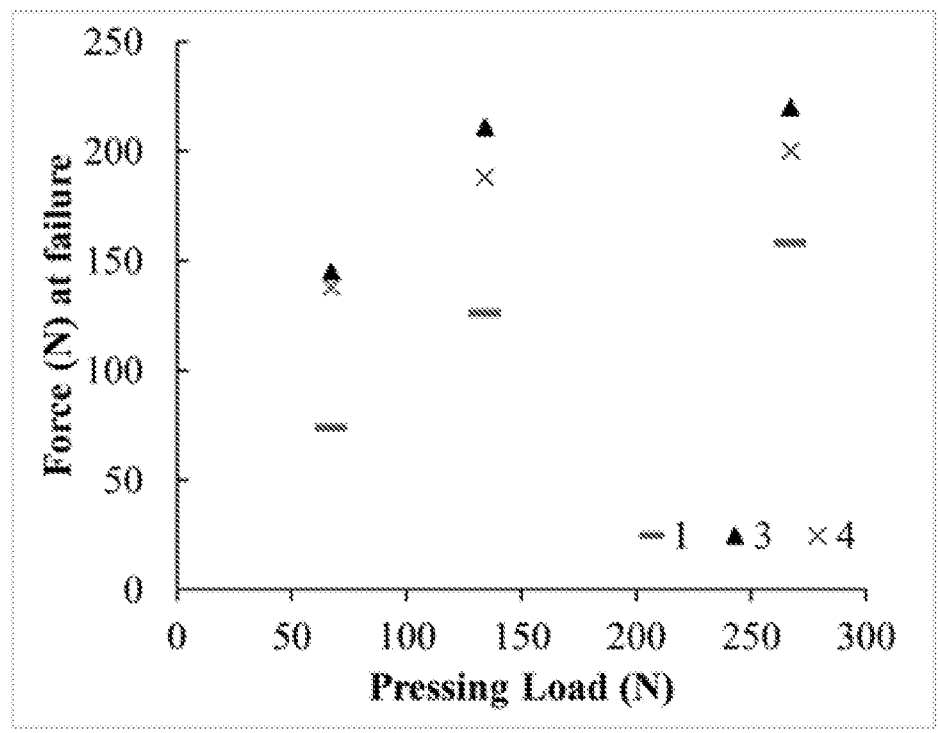
FIG. 4 is a graph showing the variation of force at failure for butt joints assembled using reversible adhesive copolymers according to the disclosure at varying pressing load (applied for 2 minutes).
Figure 5:
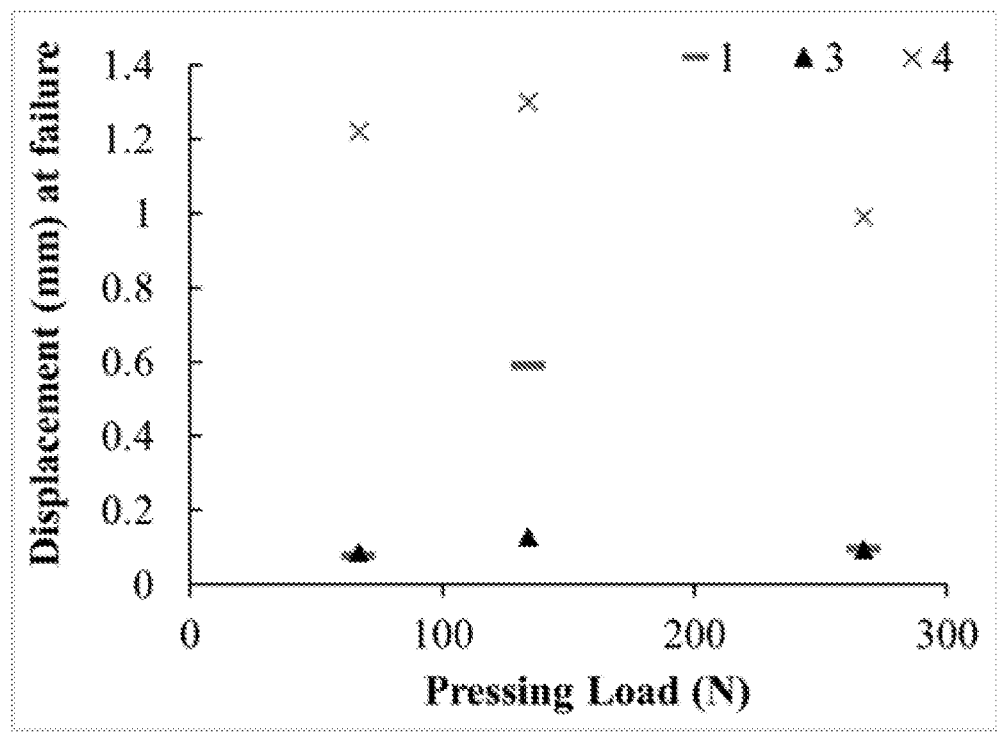
FIG. 5 is a graph showing the variation of displacement at failure for butt joints assembled using reversible adhesive copolymers according to the disclosure at varying pressing load (applied for 2 minutes).

Butt Joint Testing:

Butt joint test articles were prepared as described above using the formulated polymer adhesives. FIG. 4 shows the average force at failure and FIG. 5 shows the displacement at failure based on different pressing loads applied on butt joints during their manufacturing. On average, the force (N) to failure increased as the pressing load was increased. This was evident in all the polymer compositions used as adhesives. Butt joints manufactured using polymer 4 exhibited a similar force to failure as polymer 3 despite of the smaller MOE and tensile strength of the adhesive. Furthermore, joints manufactured using polymer 4 exhibited a higher displacement to failure (FIG. 5) due to higher toughness/strain to failure value observed for this adhesive (FIG. 3).

Figure 6:
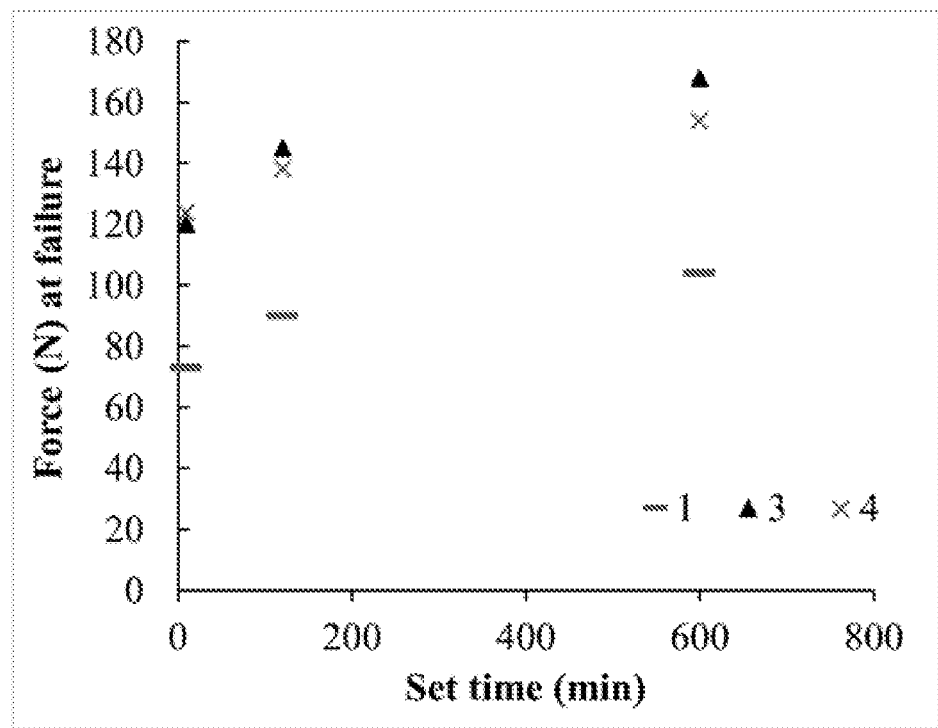
FIG. 6 is a graph showing the variation of force at failure for butt joints assembled using reversible adhesive copolymers according to the disclosure at varying set time (67N constant applied load applied for 2 minutes).
Figure 7:
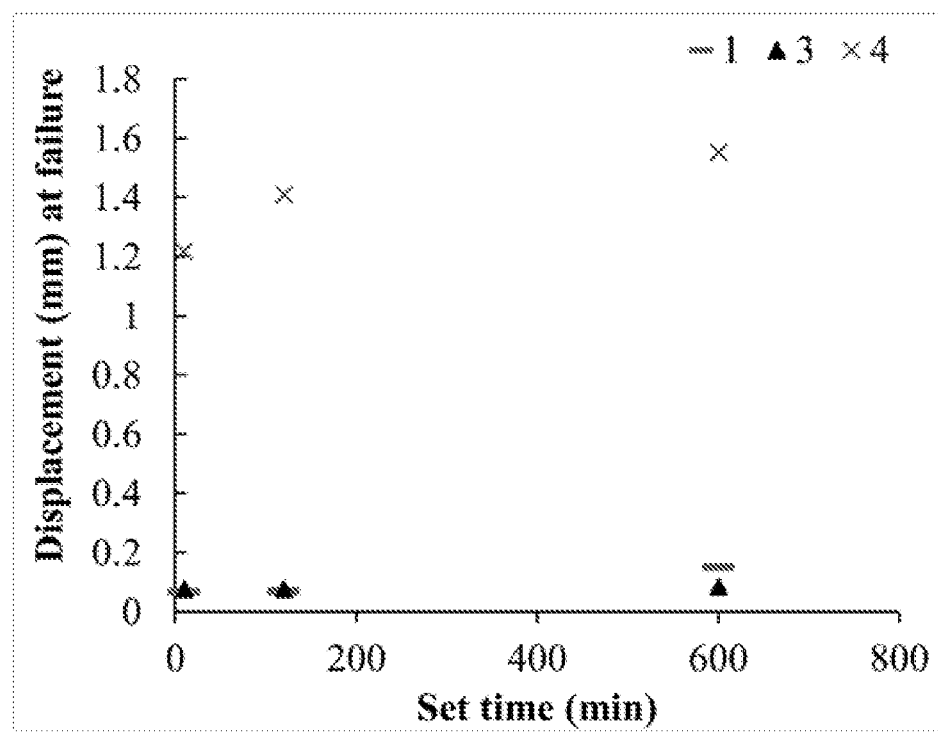
FIG. 7 is a graph showing the variation of displacement at failure for butt joints assembled using reversible adhesive copolymers according to the disclosure at varying set time (67N constant applied load applied for 2 minutes).

Like the effect of pressing load, force (N) to failure was found to increase with an increase in set time after pressing for butt joints manufactured using polymers 1, 3, and 4 with a constant pressing time of 2 minutes (FIG. 6). The set time represents allowing the specimens to remain under no load after pressing for a fixed time before performing the peel test. The adhesive strength was found to increase in polymer 1, 3, and 4 as the nBA content increased. The effect of time was minimal for butt joints manufactured using polymer 1 and 3, but polymer 4 showed an increase in displacement to failure as the set time is increased (FIG. 7). The increase in displacement to failure can be attributed to development of more non-covalent supramolecular interactions at the interface of the adhesive layers on the adherents. This can be attributed to more entanglements of the comparatively more nBA chains which need more time to rearrange into its best fit key and lock configuration. The force to failure in manufactured butt joints was also converted into butt joints strengths (MPa) and is shown for varying loads in Table 1 and for varying set times in Table 2. Table 1 shows butt joints strength in MPa units with varying loads in dwell time, where the three different loads of 15 lbs (67N), 30 lbs (134N) and 60 lbs (267N) were applied for 2 minutes and the set time was 10 minutes. Table 2 shows butt joints strength in MPa units with varying set times, where loads of 15 lbs (67N) were applied for 2 minutes, and the set time was 10, 120, or 600 minutes.

TABLE 1

Effect on butt joint strength with varying loads during pressing

| | Butt Joint Strength (MPa at Yield) | | | |
| Polymer | 10 min and 15 lbs (67 N) load applied | 10 min and 30 lbs (134) load applied | 10 min and 60 lbs (267 N) load applied | Cohesive strength (MPa) |
| --- | --- | --- | --- | --- |
| 1 | 0.45 | 0.79 | 0.98 | 3.75 |
| 3 | 0.74 | 1.31 | 1.364 | 2.05 |
| 4 | 0.77 | 1.17 | 1.24 | 0.15 |

TABLE 2

Effect on butt joint strength with varying set times

| | Butt Joint Strength (MPa at Yield) | | |
| Polymer | 10 min and 15 lbs (67 N) load applied | 120 min and 15 lbs (67) load applied | 600 min and 15 lbs (67) load applied |
| --- | --- | --- | --- |
| 1 | 0.45 | 0.48 | 0.65 |
| 3 | 0.74 | 0.9 | 0.98 |
| 4 | 0.77 | 0.85 | 0.96 |

In general, the adhesive strength in the manufactured joints was found to increase as the nBA content was increased in the copolymer. Although polymer 3 had less nBA content than polymer 4, it tolerated slightly higher force to failure than polymer 4. On the other hand, polymer 4 showed more strain at failure than polymer 3. Polymer 4 showed excellent tackiness properties as compared to polymer 1 and 3. The more nBA content in polymer 4 lowered its glass transition temperature (Tg), which helped in chain mobility to be locked in best configuration, and allowing it to develop more non-covalent secondary interactions. This illustrates that applying more load on joints facilitates more nBA chains coming in contact to increase the proportion of intermolecular force. Similarly, the increase in set time improved the intermolecular interactions by allowing the polymer chains to adopt their best conformations for better interactions. Depending upon the manufacturing parameters such as time and pressing loads, desired joint properties can be attained.

Figure 8:
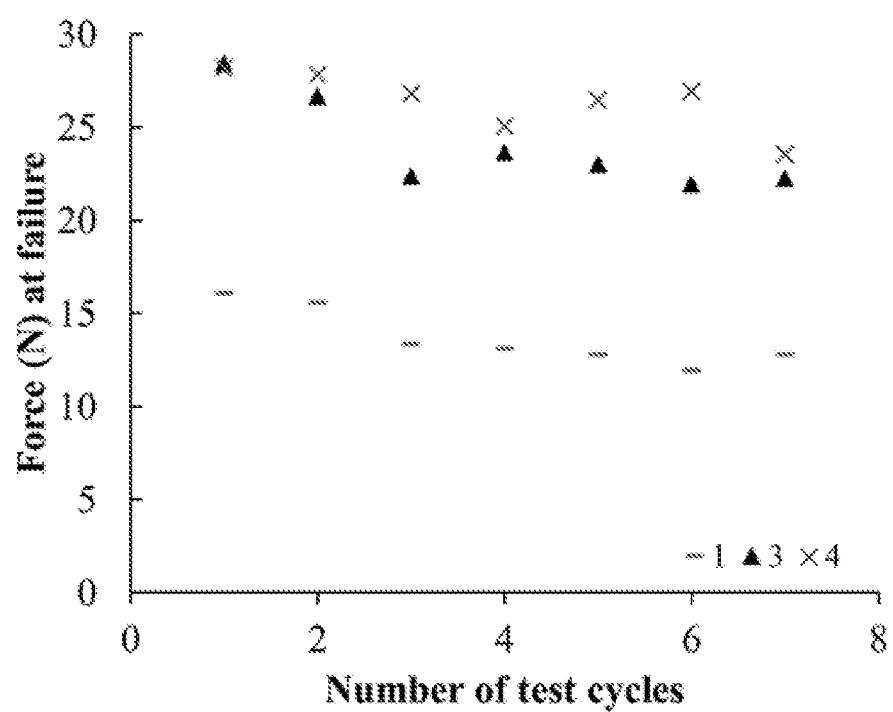
FIG. 8 is a graph showing the variation of force at failure for butt joints assembled using reversible adhesive copolymers according to the disclosure at sequential bonding/debonding cycles.
Figure 9:
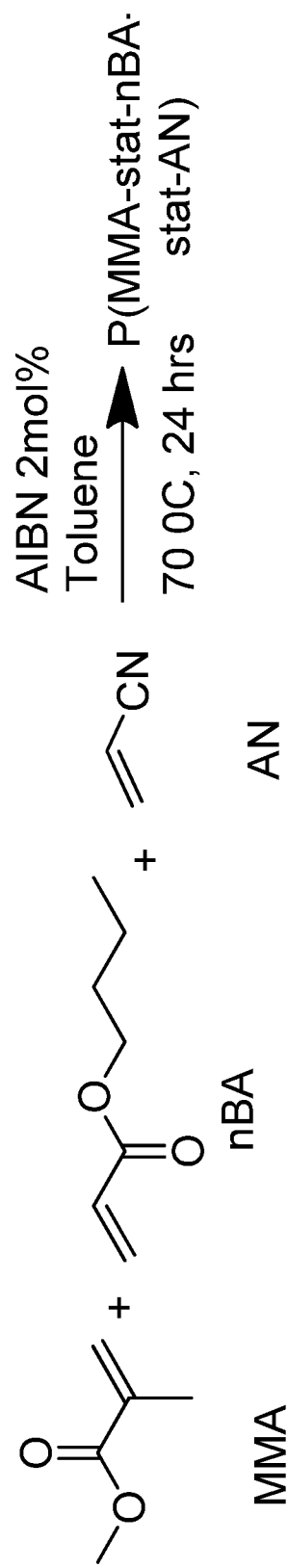
FIG. 9 is a reaction scheme illustrating the synthesis and composition of reversible adhesive copolymers according to the disclosure.

Repeatability Testing:

Butt joint test articles de-bonded after every test cycle were re-bonded back as described above to evaluate the reusability of the processed polymer as an adhesive. FIG. 8 shows the load to failure of butt joints manufactured using polymers 1, 3, and 4 after several test cycles of de-bonding/re-bonding. On average, the load to failure decreased by ~15% after 7 test cycles for polymer 1 and 3, and polymer 4 exhibited even better reusability. The repeatability tests were carried out at a press load of 15 lbs (67N) for 2 mins while the set time after load release was 10 mins.

Example 2—Poly(PMMA/nBA/AN) Reversible Adhesive

The example illustrates a reversible adhesive including poly(methacrylate-stat-n-butyl acrylate-stat-acrylonitrile) (PMMA/nBA/AN) copolymers according to the disclosure as well as articles including reversibly joined surfaces or substrates using the reversible adhesives. The reversible adhesive copolymers we formed as above for Example 1, with the difference being that acrylonitrile (AN) was added as a third vinyl monomer for the copolymer. The adhesive properties were similarly tested as in Example 1, with the formation of butt joint test articles and evaluation of their mechanical properties. Polymer 1 of Example 2 was analogous to polymer 4 of Example 4, having a 35:65 mole ratio for MMA:nBA and not including any AN as a third comonomer. Polymer 2 of Example 2 included the AN cononomer in relative molar amounts of 32.5:62.5:5 for MMA:nBA:AN. Polymer 2 had a number-average molecular weight (Mn) of 25908 g/mol and a weight-average molecular weight (Mw) of 78990 g/mol. Incorporation of the AN comonomer unit into polymer 2 was confirmed by $^1$H NMR as above for Example 1.

Butt joint articles were assembled and tested using both polymer 1 (without AN) and polymer 2 (with AN) using the same procedures from Example 1. Addition of the small amount of AN comonomer in polymer 2 resulted significantly stronger adhesive strength relative to the polymer 1 analog (without AN). This example demonstrates that additional comonomers can be added to the vinyl spacer monomer and the vinyl reversible binder monomer (e.g., MMA and nBA in this case) to control or otherwise modify the physical, chemical, and/or mechanical properties of the copolymer while still retaining the reversible adhesive functionality of he copolymer.

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the compositions, processes, kits, or apparatus are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

What is claimed is:

1. An article comprising:
   a first surface;
   a second surface different from the first surface; and
   a reversible adhesive composition in contact with and bonded to the first surface and the second surface at an interface of the article, wherein the reversible adhesive composition comprises a copolymer comprising:
   a vinyl spacer monomer unit comprising at least one of (i) a pendant carboxylate group with a carbonyl carbon backbone attachment and in the form of an acid, a salt, an ester with 1 to 3 carbon atoms in a corresponding ester group, and combinations thereof, (ii) a pendant carboxylate group with an ester oxygen backbone attachment and having a hydrocarbon tail group with 1 to 3 carbon atoms, (iii) a pendant ether group with an ether oxygen backbone attachment and having a hydrocarbon tail group with 1 to 3 carbon atoms; and
   a vinyl reversible binder monomer unit comprising at least one of (i) a pendant carboxylate group with a carbonyl carbon backbone attachment and in the form of an ester having 3 to 20 carbon atoms in a corresponding ester group, (ii) a pendant carboxylate group with an ester oxygen backbone attachment and having a hydrocarbon tail group with 3 to 20 carbon atoms, and (iii) a pendant ether group with an ether oxygen backbone attachment and having a hydrocarbon tail group with 3 to 20 carbon atoms;
   wherein the vinyl spacer monomer unit and the vinyl reversible binder monomer unit are different.

2. The article of claim 1, wherein:
   the first surface and the second surface are capable of being separated from each other (i) without damage to the first surface or the second surface, and (ii) with at least a portion of the reversible adhesive composition remaining each of the first surface and the second surface; and
   the separated first surface and the separated second surface are capable of being rejoined at the interface with the reversible adhesive composition in contact with and bonded to the first surface and the second surface at the interface.

3. The article of claim 1, wherein:
   the vinyl spacer monomer unit has a structure corresponding to a polymerization product of a vinyl spacer monomer according to formula I.A:

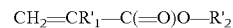

$$CH_2=CR'_1-C(=O)O-R'_2 \qquad (I.A)$$

where:
R'$_1$ is selected from hydrogen (H) and a methyl group; and
R'$_2$ is selected from hydrogen (H), an alkali metal, and hydrocarbons containing from 1 to 3 carbon atoms.

4. The article of claim 1, wherein:
the vinyl spacer monomer unit has a structure corresponding to a polymerization product of a vinyl spacer monomer according to formula II.A:

$$CH_2=CR'_3-OC(=O)-R'_4 \qquad (II.A)$$

where:
R'$_3$ is selected from hydrogen (H) and a methyl group; and
R'$_4$ is selected from hydrocarbons containing from 1 to 3 carbon atoms.

5. The article of claim 1, wherein:
the vinyl spacer monomer unit has a structure corresponding to a polymerization product of a vinyl spacer monomer according to formula III.A:

$$CH_2=CR'_5-O-R'_6 \qquad (III.A)$$

where:
R'$_5$ is selected from hydrogen (H) and a methyl group; and
R'$_6$ is selected from hydrocarbons containing from 1 to 3 carbon atoms.

6. The article of claim 1, wherein:
the vinyl reversible binder monomer unit has a structure corresponding to a polymerization product of a vinyl reversible binder monomer according to formula I.B:

$$CH_2=CR_1-C(=O)O-R_2 \qquad (I.B)$$

where:
R$_1$ is selected from hydrogen (H) and a methyl group; and
R$_2$ is selected from hydrocarbons containing from 3 to 20 carbon atoms.

7. The article of claim 1, wherein:
the vinyl reversible binder monomer unit has a structure corresponding to a polymerization product of a vinyl reversible binder monomer according to formula II.B:

$$CH_2=CR_3-OC(=O)-R_4 \qquad (II.B)$$

where:
R$_3$ is selected from hydrogen (H) and a methyl group; and
R$_4$ is selected from hydrocarbons containing from 3 to 20 carbon atoms.

8. The article of claim 1, wherein:
the vinyl reversible binder monomer unit has a structure corresponding to a polymerization product of a vinyl reversible binder monomer according to formula III.B:

$$CH_2=CR_5-O-R_6 \qquad (III.B)$$

where:
R$_5$ is selected from hydrogen (H) and a methyl group; and
R$_6$ is selected from hydrocarbons containing from 3 to 20 carbon atoms.

9. The article of claim 1, wherein:
the vinyl spacer monomer units are present in the copolymer in a range from 10 mol. % to 90 mol. % relative to total vinyl spacer monomer units and vinyl reversible binder monomer units combined; and
the vinyl reversible binder monomer units are present in the copolymer in a range from 10 mol. % to 90 mol. % relative to total vinyl spacer monomer units and vinyl reversible binder monomer units combined.

10. The article of claim 1, wherein the copolymer further comprises:
a vinyl crosslinking monomer unit (e.g., as a third monomer unit); and
crosslinks between copolymer chains via the vinyl crosslinking monomer unit.

11. The article of claim 1, wherein the copolymer of the reversible adhesive composition comprises statistical segments with the vinyl spacer monomer units and the vinyl reversible binder monomer unit.

12. The article of claim 1, wherein the copolymer of the reversible adhesive composition comprises alternating segments between the vinyl spacer monomer units and the vinyl reversible binder monomer unit.

13. The article of claim 1, wherein the copolymer of the reversible adhesive composition has a glass transition temperature in a range from −10° C. to 18° C.

14. The article of claim 1, wherein the copolymer of the reversible adhesive composition has a molecular weight in a range from 1500 g/mol to 2,000,000 g/mol.

15. The article of claim 1, wherein the reversible adhesive composition has a thickness between the first surface and the second surface in a range from 0.005 μm to 5000 μm.

16. The article of claim 1, wherein the reversible adhesive composition further comprises an additive selected from the group consisting of a physical crosslinking agent, an adhesion promoter, and combinations thereof.

17. The article of claim 1, wherein:
the first surface is a surface of a first substrate; and
the second surface is a surface of a second substrate separate from the first substrate.

18. The article of claim 1, wherein the first surface and the second surface are surfaces of a single substrate.

19. The article of claim 1, wherein the first surface and the second surface are formed from different materials.

20. The article of claim 1, wherein the first surface and the second surface are formed from the same material.

21. The article of claim 1, wherein any substrates in the article are independently selected from the group of metal and alloys, plastics, polymers, composites, glass, wood, fabric, paper substrate, organic-inorganic hybrid substrates, and ceramics.

22. A method for forming the article of claim 1, the method comprising:
providing a first surface comprising at least a portion of the reversible adhesive composition of claim 1 thereon;
providing a second surface different from the first surface and comprising at least a portion of the reversible adhesive composition of claim 1 thereon; and
contacting the reversible adhesive composition of the first surface with the reversible adhesive composition of the second surface at an interface for a time and at a pressure sufficient to bond the first surface and the second surface together at the interface with the reversible adhesive composition there between, thereby forming the article of claim 1.

23. A method for de-bonding and optionally re-bonding the article of claim 1, the method comprising:
providing the article of claim 1; and
applying a force sufficient to separate the first surface from the second surface while retaining at least a portion of the reversible adhesive composition on each of the first surface and the second surface.

24. The method of claim 23, further comprising:
contacting the reversible adhesive composition of the separated first surface with the reversible adhesive composition of the separated second surface at an interface for a time and pressure sufficient to re-bond the first surface and the second surface together at the interface with the reversible adhesive composition therebetween, thereby re-forming the article of claim 1.

\* \* \* \* \*